(12) United States Patent
Laine et al.

(10) Patent No.: US 11,291,558 B2
(45) Date of Patent: Apr. 5, 2022

(54) DYNAMIC IMPLANT FIXATION PLATE

(71) Applicant: NANOHIVE MEDICAL LLC, Woburn, MA (US)

(72) Inventors: Christopher Laine, Bellingham, MA (US); Ian Helmar, Beverly, MA (US); Lucas Diehl, Beverly, MA (US); Jason Tinley, Fort Worth, TX (US); Kevin D. Chappuis, Malden, MA (US); John F. Sullivan, Pelham, NH (US); Christine Emery, Somerville, MA (US)

(73) Assignee: NANOHIVE MEDICAL LLC, Woburn, MA (US)

( * ) Notice: Subject to any disclaimer, the term of this patent is extended or adjusted under 35 U.S.C. 154(b) by 0 days.

(21) Appl. No.: 16/523,962

(22) Filed: Jul. 26, 2019

(65) Prior Publication Data
US 2020/0038069 A1 Feb. 6, 2020

Related U.S. Application Data

(60) Provisional application No. 62/703,562, filed on Jul. 26, 2018.

(51) Int. Cl.
| | | |
|---|---|---|
| *A61F 2/44* | (2006.01) |
| *A61B 17/70* | (2006.01) |
| *A61B 17/86* | (2006.01) |
| *A61B 17/80* | (2006.01) |
| *A61F 2/30* | (2006.01) |

(52) U.S. Cl.
CPC .......... *A61F 2/447* (2013.01); *A61B 17/7059* (2013.01); *A61B 17/8023* (2013.01); *A61B 17/8047* (2013.01); *A61B 17/86* (2013.01); *A61F 2002/30578* (2013.01)

(58) Field of Classification Search
CPC .......... A61F 2/44; A61F 2/442; A61F 2/4455; A61F 2/446; A61F 2/4465; A61F 2/447; A61F 2002/444
See application file for complete search history.

(56) References Cited

U.S. PATENT DOCUMENTS

| 5,059,193 A | 10/1991 | Kuslich |
| 5,615,528 A | 4/1997 | Owens |
| 5,674,294 A | 10/1997 | Bainville et al. |

(Continued)

FOREIGN PATENT DOCUMENTS

| CN | 204971711 U | 1/2016 |
| EP | 1506753 A1 | 2/2005 |

(Continued)

OTHER PUBLICATIONS

U.S. Appl. No. 15/615,227, filed Jun. 6, 2017, Christopher L. Jones.

(Continued)

*Primary Examiner* — Eric S Gibson
(74) *Attorney, Agent, or Firm* — White & Case LLP

(57) ABSTRACT

The dynamic implant fixation plate and implant configured to accept the disclosed fixation plate can, in some aspects, provide a means of fixing an implant relative one or more planes while allowing motion relative to one or more planes. The use of the disclosed fixation plate and corresponding implant can reduce the occurrence of stress shielding and permit enhanced loading of the implant site.

13 Claims, 17 Drawing Sheets

(56) References Cited

U.S. PATENT DOCUMENTS

| | | | |
|---|---|---|---|
| 6,149,688 A | 11/2000 | Brosnahan et al. | |
| 6,206,924 B1 | 3/2001 | Timm | |
| 6,723,126 B1 | 4/2004 | Berry | |
| 6,767,594 B1 | 7/2004 | Miroshin et al. | |
| 6,902,579 B2 | 6/2005 | Harms et al. | |
| 7,128,760 B2 | 10/2006 | Michelson | |
| 7,172,627 B2 * | 2/2007 | Fiere | A61F 2/4611 623/17.11 |
| 7,217,293 B2 | 5/2007 | Branch, Jr. | |
| 7,637,950 B2 | 12/2009 | Baccelli et al. | |
| D619,255 S | 7/2010 | Richter et al. | |
| 7,799,079 B2 | 9/2010 | Hestad et al. | |
| D626,233 S | 10/2010 | Cipoletti et al. | |
| 7,850,731 B2 | 12/2010 | Brittan et al. | |
| 8,043,381 B2 | 10/2011 | Hestad et al. | |
| D653,757 S | 2/2012 | Binder | |
| 8,236,058 B2 | 8/2012 | Fabian et al. | |
| 8,425,576 B2 * | 4/2013 | Anderson | A61B 17/7059 606/289 |
| D682,427 S | 5/2013 | Farris et al. | |
| D692,136 S | 10/2013 | Tyber | |
| 8,663,332 B1 | 3/2014 | To et al. | |
| 8,697,231 B2 | 4/2014 | Longepied et al. | |
| 8,740,983 B1 | 6/2014 | Arnold et al. | |
| D708,747 S | 7/2014 | Curran et al. | |
| D711,537 S | 8/2014 | Pimenta et al. | |
| 8,900,307 B2 | 12/2014 | Hawkins et al. | |
| 8,945,227 B2 * | 2/2015 | Kirschman | A61B 17/70 623/17.16 |
| 9,005,291 B2 | 4/2015 | Loebl et al. | |
| D737,446 S | 8/2015 | Butler et al. | |
| 9,155,819 B2 | 10/2015 | Fonte et al. | |
| 9,186,257 B2 * | 11/2015 | Geisler | A61F 2/442 |
| D750,249 S | 2/2016 | Grimberg, Jr. et al. | |
| 9,271,836 B2 * | 3/2016 | Pavento | A61B 17/7059 |
| 9,271,843 B2 | 3/2016 | Fabian et al. | |
| 9,308,076 B2 | 4/2016 | Ringeisen et al. | |
| 9,456,901 B2 | 10/2016 | Jones et al. | |
| 9,492,285 B2 | 11/2016 | Saidha et al. | |
| 9,566,163 B2 | 2/2017 | Suddaby et al. | |
| 9,662,225 B2 * | 5/2017 | Pavento | A61B 17/7059 |
| D789,539 S | 6/2017 | Kleiner et al. | |
| 9,668,877 B2 * | 6/2017 | Pavento | A61F 2/442 |
| 9,872,781 B2 * | 1/2018 | Pavento | A61F 2/4455 |
| D816,844 S | 5/2018 | Ricca et al. | |
| 9,962,269 B2 | 5/2018 | Jones et al. | |
| 10,045,797 B1 * | 8/2018 | Walkenhorst | A61F 2/447 |
| D833,012 S | 11/2018 | Jones et al. | |
| D833,611 S | 11/2018 | Jones et al. | |
| D833,612 S | 11/2018 | Jones et al. | |
| 10,130,488 B2 | 11/2018 | Saidha et al. | |
| D835,279 S | 12/2018 | Jones et al. | |
| D835,788 S | 12/2018 | Jones et al. | |
| D840,036 S | 2/2019 | Jones et al. | |
| 10,368,997 B2 | 8/2019 | Jones et al. | |
| 10,405,983 B2 | 9/2019 | Jones et al. | |
| 2002/0161444 A1 | 10/2002 | Choi | |
| 2003/0114936 A1 | 6/2003 | Sherwood et al. | |
| 2004/0162618 A1 | 8/2004 | Mujwid et al. | |
| 2004/0243241 A1 | 12/2004 | Istephanous | |
| 2004/0258732 A1 | 12/2004 | Shikinami | |
| 2005/0049706 A1 | 3/2005 | Brodke et al. | |
| 2005/0101960 A1 * | 5/2005 | Fiere | A61F 2/4611 623/17.11 |
| 2005/0113916 A1 | 5/2005 | Branch | |
| 2005/0129726 A1 | 6/2005 | Liebschner | |
| 2005/0159813 A1 * | 7/2005 | Molz | A61F 2/447 623/17.11 |
| 2005/0251083 A1 | 11/2005 | Carr-Brendel et al. | |
| 2006/0147332 A1 | 7/2006 | Jones et al. | |
| 2006/0257817 A1 | 11/2006 | Shelton | |
| 2006/0259144 A1 | 11/2006 | Trieu | |
| 2006/0276925 A1 | 12/2006 | Lin et al. | |
| 2007/0073398 A1 | 3/2007 | Fabian et al. | |
| 2007/0123987 A1 | 5/2007 | Bernstein | |
| 2007/0142914 A1 | 6/2007 | Jones et al. | |
| 2007/0150068 A1 | 6/2007 | Dong et al. | |
| 2007/0233247 A1 | 10/2007 | Schwab | |
| 2007/0270858 A1 | 11/2007 | Trieu et al. | |
| 2008/0161925 A1 * | 7/2008 | Brittan | A61F 2/4465 623/17.16 |
| 2008/0161927 A1 | 7/2008 | Savage et al. | |
| 2008/0169585 A1 | 7/2008 | Zinniel | |
| 2008/0269903 A1 | 10/2008 | Francis et al. | |
| 2008/0294262 A1 * | 11/2008 | Levieux | A61F 2/4611 623/17.16 |
| 2008/0300634 A1 * | 12/2008 | Gray | A61B 17/7059 606/280 |
| 2008/0306596 A1 | 12/2008 | Jones et al. | |
| 2008/0306609 A1 | 12/2008 | Lee et al. | |
| 2009/0012529 A1 * | 1/2009 | Blain | A61F 2/4611 606/99 |
| 2009/0037148 A1 | 2/2009 | Lin et al. | |
| 2009/0105831 A1 * | 4/2009 | Jones | A61B 17/8042 623/17.16 |
| 2009/0182429 A1 | 7/2009 | Humphreys et al. | |
| 2009/0287214 A1 | 11/2009 | Yu | |
| 2009/0317278 A1 | 12/2009 | Kokubo | |
| 2009/0326580 A1 * | 12/2009 | Anderson | A61B 17/8047 606/246 |
| 2010/0087925 A1 | 4/2010 | Kostuik et al. | |
| 2010/0100185 A1 | 4/2010 | Trieu et al. | |
| 2010/0145459 A1 | 6/2010 | McDonough et al. | |
| 2010/0234948 A1 | 9/2010 | Khoury et al. | |
| 2010/0286783 A1 | 11/2010 | Lechmann et al. | |
| 2011/0004307 A1 | 1/2011 | Ahn et al. | |
| 2011/0012280 A1 | 1/2011 | Deslauriers et al. | |
| 2011/0029084 A1 | 2/2011 | Milbocker et al. | |
| 2011/0029087 A1 | 2/2011 | Haider et al. | |
| 2011/0144764 A1 | 6/2011 | Bagga et al. | |
| 2011/0190892 A1 * | 8/2011 | Kirschman | A61F 2/447 623/17.16 |
| 2011/0224796 A1 | 9/2011 | Weiland et al. | |
| 2011/0282392 A1 | 11/2011 | Murphy et al. | |
| 2012/0022653 A1 | 1/2012 | Kirschman | |
| 2012/0123546 A1 | 5/2012 | Medina | |
| 2012/0150299 A1 | 6/2012 | Ergun et al. | |
| 2012/0177939 A1 | 7/2012 | Longepied et al. | |
| 2012/0179258 A1 | 7/2012 | Glazer et al. | |
| 2012/0185047 A1 | 7/2012 | Wooley | |
| 2012/0215310 A1 | 8/2012 | Sharp et al. | |
| 2012/0215313 A1 | 8/2012 | Saidha et al. | |
| 2012/0303128 A1 | 11/2012 | Ullrich, Jr. et al. | |
| 2012/0312779 A1 | 12/2012 | Patterson et al. | |
| 2012/0321878 A1 | 12/2012 | Landon et al. | |
| 2013/0026492 A1 | 1/2013 | Khan | |
| 2013/0039094 A1 | 2/2013 | Kolb et al. | |
| 2013/0060337 A1 * | 3/2013 | Petersheim | A61B 17/8042 623/17.16 |
| 2013/0073044 A1 * | 3/2013 | Gamache | A61F 2/442 623/17.16 |
| 2013/0218276 A1 | 8/2013 | Fiechter et al. | |
| 2013/0238095 A1 * | 9/2013 | Pavento | A61F 2/442 623/17.16 |
| 2013/0282126 A1 | 10/2013 | Saidha et al. | |
| 2013/0310939 A1 | 11/2013 | Fabian et al. | |
| 2013/0325129 A1 | 12/2013 | Huang | |
| 2014/0012382 A1 | 1/2014 | Doty | |
| 2014/0012384 A1 * | 1/2014 | Kana | A61F 2/30744 623/17.16 |
| 2014/0037873 A1 | 2/2014 | Cheung et al. | |
| 2014/0046447 A1 * | 2/2014 | Dunworth | A61F 2/4455 623/17.16 |
| 2014/0046448 A1 * | 2/2014 | Kana | A61F 2/4455 623/17.16 |
| 2014/0107786 A1 | 4/2014 | Geisler et al. | |
| 2014/0121776 A1 | 5/2014 | Hunt | |
| 2014/0277482 A1 | 9/2014 | Gfeller et al. | |
| 2015/0005885 A1 | 1/2015 | Zhang et al. | |
| 2015/0025635 A1 | 1/2015 | Laubert | |
| 2015/0093283 A1 | 4/2015 | Miller et al. | |

(56) References Cited

U.S. PATENT DOCUMENTS

| | | | |
|---|---|---|---|
| 2015/0100126 A1* | 4/2015 | Melkent | A61F 2/442 623/17.16 |
| 2015/0360421 A1 | 12/2015 | Burhop et al. | |
| 2016/0000574 A9 | 1/2016 | Fabian et al. | |
| 2016/0022431 A1 | 1/2016 | Wickham | |
| 2016/0027425 A1 | 1/2016 | Cook et al. | |
| 2016/0038301 A1 | 2/2016 | Wickham | |
| 2016/0058480 A1* | 3/2016 | Laubert | A61F 2/4611 606/289 |
| 2016/0085882 A1 | 3/2016 | Li et al. | |
| 2016/0113775 A1 | 4/2016 | Willis et al. | |
| 2016/0166284 A1 | 6/2016 | Hacking et al. | |
| 2016/0184103 A1 | 6/2016 | Fonte et al. | |
| 2016/0199193 A1 | 7/2016 | Willis et al. | |
| 2016/0206440 A1 | 7/2016 | DeRidder et al. | |
| 2016/0235546 A1* | 8/2016 | Cheng | A61F 2/4465 |
| 2016/0270931 A1 | 9/2016 | Trieu | |
| 2017/0014235 A1 | 1/2017 | Jones et al. | |
| 2017/0020685 A1* | 1/2017 | Geisler | A61F 2/442 |
| 2017/0042698 A1 | 2/2017 | Saidha et al. | |
| 2017/0095337 A1 | 4/2017 | Pasini et al. | |
| 2017/0119538 A1 | 5/2017 | Baynham | |
| 2017/0312096 A1* | 11/2017 | Liu | A61F 2/4455 |
| 2017/0325966 A1* | 11/2017 | Capote | A61B 17/8042 |
| 2017/0348114 A1 | 12/2017 | Jones et al. | |
| 2017/0367845 A1 | 12/2017 | Eisen et al. | |
| 2018/0092752 A1 | 4/2018 | Williams | |
| 2018/0140427 A1 | 5/2018 | Conway et al. | |
| 2018/0221156 A1 | 8/2018 | Jones et al. | |
| 2018/0228570 A1 | 8/2018 | Jones et al. | |
| 2018/0228612 A1 | 8/2018 | Jones et al. | |
| 2018/0228613 A1 | 8/2018 | Jones et al. | |
| 2018/0243094 A1 | 8/2018 | Jones et al. | |
| 2018/0243097 A1 | 8/2018 | Jones et al. | |
| 2018/0280139 A1 | 10/2018 | Jones et al. | |
| 2018/0280140 A1 | 10/2018 | Jones et al. | |
| 2018/0280141 A1 | 10/2018 | Jones et al. | |
| 2018/0280144 A1 | 10/2018 | Jones et al. | |
| 2018/0280145 A1 | 10/2018 | Jones et al. | |
| 2018/0296350 A1 | 10/2018 | Hamzey et al. | |
| 2018/0318099 A1* | 11/2018 | Altarac | A61F 2/4455 |
| 2018/0318100 A1* | 11/2018 | Altarac | A61F 2/4455 |
| 2018/0368990 A1 | 12/2018 | Saidha et al. | |
| 2018/0368992 A1* | 12/2018 | Zink | A61B 90/39 |
| 2019/0133778 A1* | 5/2019 | Johnston | A61F 2/442 |
| 2019/0133783 A1 | 5/2019 | Unger et al. | |
| 2019/0150910 A1 | 5/2019 | Jones et al. | |
| 2019/0209215 A1* | 7/2019 | Baynham | A61B 17/7059 |
| 2019/0250438 A1 | 8/2019 | Oton et al. | |
| 2019/0343638 A1 | 11/2019 | Jones et al. | |
| 2019/0343644 A1 | 11/2019 | Ryan et al. | |
| 2020/0000595 A1 | 1/2020 | Jones et al. | |
| 2020/0038069 A1* | 2/2020 | Jones | A61F 2/447 |
| 2020/0138595 A1* | 5/2020 | Shoshtaev | A61F 2/4611 |
| 2020/0281736 A1* | 9/2020 | Milz | A61F 2/447 |

FOREIGN PATENT DOCUMENTS

| | | |
|---|---|---|
| EP | 2647453 A2 | 10/2013 |
| EP | 1887954 B1 | 9/2014 |
| WO | WO-1999033641 A1 | 7/1999 |
| WO | WO-0217823 A1 | 3/2002 |
| WO | WO-2014160389 A1 | 10/2014 |
| WO | WO-2014172495 A2 | 10/2014 |
| WO | WO-2015164982 A1 | 11/2015 |
| WO | WO-2016061148 A1 | 4/2016 |
| WO | WO-2016130878 A1 | 8/2016 |
| WO | WO-2017214114 A1 | 12/2017 |
| WO | WO-2018152077 A1 | 8/2018 |
| WO | WO-2018156905 A1 | 8/2018 |
| WO | WO-2018182834 A1 | 10/2018 |
| WO | WO-2018183809 A1 | 10/2018 |
| WO | WO-2020023938 A1 | 1/2020 |

OTHER PUBLICATIONS

U.S. Appl. No. 15/942,846, filed Apr. 2, 2018, Christopher L. Jones.
U.S. Appl. No. 15/876,695, filed Jan. 22, 2018, Christopher L. Jones.
U.S. Appl. No. 15/876,793, filed Jan. 22, 2018, Christopher L. Jones.
U.S. Appl. No. 15/876,903, filed Jan. 22, 2018, Christopher L. Jones.
U.S. Appl. No. 15/877,002, filed Jan. 22, 2018, Christopher L. Jones.
U.S. Appl. No. 16/251,383, filed Jan. 18, 2019, Christopher L. Jones.
U.S. Appl. No. 16/518,281, filed Jan. 22, 2019, Christopher L. Jones.
U.S. Appl. No. 16/917,685, filed Jun. 30, 2020, Christopher L. Jones.
U.S. Appl. No. 15/895,201, filed Feb. 13, 2018, Christopher L. Jones.
U.S. Appl. No. 15/895,213, filed Feb. 13, 2018, Christopher L. Jones.
U.S. Appl. No. 15/895,228, filed Feb. 13, 2018, Christopher L. Jones.
U.S. Appl. No. 16/565,321, filed Sep. 9, 2019, Christopher L. Jones.
U.S. Appl. No. 15/903,648, filed Feb. 23, 2018, Christopher L. Jones.
U.S. Appl. No. 15/903,667, filed Feb. 23, 2018, Christopher L. Jones.
U.S. Appl. No. 15/941,193, filed Mar. 3, 2018, Christopher L. Jones.
U.S. Appl. No. 16/744,103, filed Jan. 15, 2020, Christopher L. Jones.
Ahmadi, S. et al., "Additively Manufactured Open-Cell Porous Biomaterials Made from Six Different Space-Filling Unit Cells: The Mechanical and Morphological Properties," Materials, vol. 8:1871-1896 (2015).
Babaee S., et al., "Mechanical properties of open-cell rhombic dodecahedron cellular structures," Acta Materialia, vol. 60:2873-2885 (2012).
Chandran R.; "Optimization of Support Structures in Additive Manufacturing Process", Dissertation, University of Miami, 2016 (Year:2016).
European Search Report, 17810838.7, dated Dec. 19, 2019, 8 pages.
Hoffmann, W. et al., "Rapid prototyped porous nickel-titanium scaffolds as bone substitutes," Journal of Tissue Engineering, vol. 5:1-14 (2014).
International Preliminary Report on Patentability, PCT/US2017/36111, dated Jun. 27, 2018, 26 pages.
International Search Report and Written Opinion, PCT /US2017/36111, dated Nov. 6, 2017, 10 pages.
International Search Report and Written Opinion, PCT/US2018/017919, dated Jun. 6, 2018, 14 pages.
International Preliminary Report on Patentability, PCT/US2018/017919, dated Aug. 20, 2019, 11 pages.
International Preliminary Report on Patentability, PCT/US2018/019437, dated Aug. 27, 2019, 16 pages.
International Search Report and Written Opinion, PCT/US2018/019437, dated Jun. 28, 2018, 19 pages.
International Search Report and Written Opinion, PCT/US2018/014720, dated Jun. 1, 2018, 13 pages.
International Search Report and Written Opinion, PCT/US2018/025351, dated Jun. 8, 2018, 14 pages.
International Search Report and Written Opinion, PCT/US2019/043803, dated Nov. 7, 2019, 11 pages.
Leary M., et al.; "Optimal topology for additive manufacture: A method for enabling additive manufacture of support-free optimal structures", Materials and Design, 2014, vol. 63, p. 678-690 (Year: 2014).
Nouri, A., "Titanium foam scaffolds for dental applications," Metallic Foam Bone, Chapter 5: 130-160 (2017) http://dx.doi.org/10.1016/B978-0-08-101289-5.00005-6.
Strano G., et al.; "A new approach to the design and optimization of support structures in additive manufacturing", Int. J. Adv Manufacturing Technology, 2013, 66, p. 1247-1254 (Year: 2013).

(56) References Cited

OTHER PUBLICATIONS

Stryker, "Tritanium PI Cage", Technical Data Sheet, https://www.stryker.com/builttofuse/; retrieved from wayback machine on Apr. 23, 2021; date Jun. 21, 2016.

Zhang, X., et al., "Additively Manufactured Scaffolds for Bone Tissue Engineering and the Prediction of their Mechanical Behavior: A Review," Materials, 10(10): 1-28 (2017).

U.S. Appl. No. 16/518,281, filed Jul. 22, 2019, Christopher L. Jones.

* cited by examiner

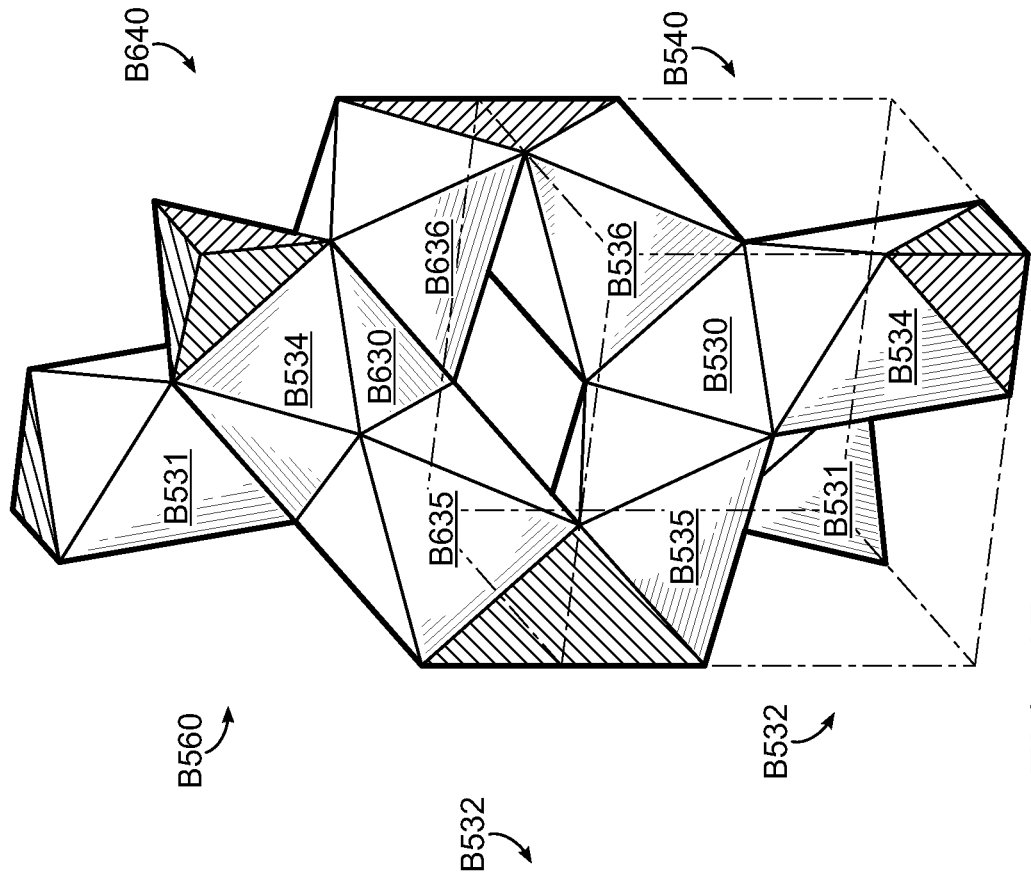
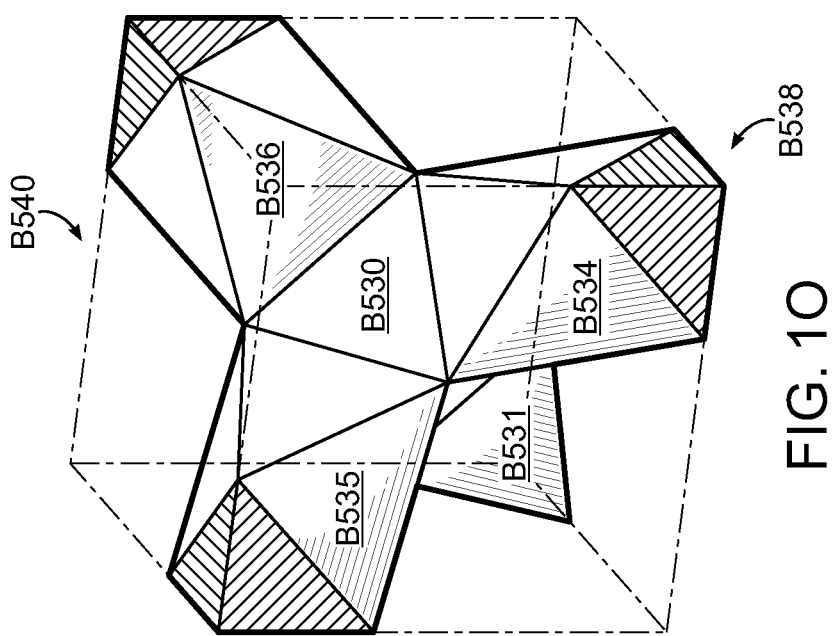

US 11,291,558 B2

DYNAMIC IMPLANT FIXATION PLATE

CROSS REFERENCE TO RELATED APPLICATIONS

This application claims the benefit of U.S. Provisional Patent Application No. 62/703,562 filed Jul. 26, 2018, which is hereby incorporated by reference in its entirety.

FIELD OF THE INVENTION

The present invention relates to medical implants, and in particular to medical implants using a fixation plate.

BACKGROUND OF THE INVENTION

Medical implants can be implanted in a fixed position within a body through a variety of means. For example, bone fusion implants may be anchored to a patient's bone through the use of a bone screw.

BRIEF SUMMARY OF THE INVENTION

Disclosed herein is a dynamic implant fixation plate (hereinafter "fixation plate") that can, in some embodiments, allow motion relative to an implant after implantation. In some embodiments, the fixation plate can rotate or move relative to an implant and/or relative to a patient's tissue after implantation. In some embodiments, the fixation plate can allow axial compression relative to an implant after implantation. As used herein, the term "tissue" refers to any type of biological, natural or synthetic, tissue, including but not limited to muscle tissue, epithelial tissue, connective tissue, nervous tissue and bony structures.

In the embodiment of the fixation plate presented, the fixation plate can be attached to the implant so that the fixation plate has at least one degree of freedom relative to the implant. As used herein, a "degree of freedom" refers to a direction in which independent motion may occur, however small that motion may be. The fixation plate can also be attached to a first bone and/or a second bone, each attachment with at least one degree of freedom. In some embodiments, the fixation plate can be attached to an implant and/or tissue so that the fixation plate has more than one degree of freedom relative to its respective attachment point. In some embodiments, the fixation plate can be attached to a first bone and/or a second bone with a conical degree of freedom.

Some embodiments of the fixation plate have screw holes with a concave profile and are attached to a patient's bone using a bone screw with a screw head having a convex profile, corresponding to the concave profile of the screw holes, when viewed from the side on the end of the screw head oriented towards the threaded portion. The use of a screw head with a convex profile and a screw hole with a concave profile can provide a fixation with at least a conical degree of freedom. The bone screw head can also be fixed relative to the fixation plate screw holes with a clearance fit of greater than zero that can provide, in some respects, an amount of translational motion and prevent binding between the bone screw head and fixation plate screw holes.

The fixation plate can be attached to an implant using a fastening means with at least one degree of freedom. Some embodiments of the fixation plate use a fastening means with a clearance fit of greater than zero between the fixation plate and an implant that can provide, in some respects, an amount of translational motion and prevent binding between the fixation plate, the implant and/or the fastening means. Some fastening means that could be used include, but are not limited to, quarter turn fasteners, screws, etc.

The fixation plate can be configured for use in bone fusion implants where an implant is fixed to one or more bony structures. Attached using anchors that allow at least one degree of freedom, the fixation plate does not significantly hinder axial compression relative to the implant, where axial relative to the implant is the direction between a first bone and a second bone. Some embodiments use at least a conical degree of freedom to allow loading beyond that purely in the axial direction.

The disclosed fixation plate can be used in situations where it is desirable to avoid stress shielding an implant. The use of a rigid attachment between an implant and a patient's bone can shield the new bone growth and existing bone from stress, resulting in weaker new bone growth and possible bone loss. The disclosed fixation plates transfer the load to the implant, rather than carrying the load, ensuring that the implant's modulus of elasticity and footprint largely determines the amount of axial compression allowed at the implant site.

Despite allowing axial movement, the disclosed fixation plate can adequately prevent lateral or fore and aft movement. When used with an implant that provides sufficient axial stability for new bone growth, the disclosed fixation plate can provide adequate stability in directions other than the axial to permit new bone to grow.

BRIEF DESCRIPTION OF THE SEVERAL VIEWS OF THE DRAWINGS

FIG. 1O is an isometric view of a sub-unit cell comprised of a single node and four struts.

FIG. 1P is an isometric view of two sub-unit cells in a stacked formation where the upper sub-unit cell is inverted and fixed to the top of the lower sub-unit cell.

DETAILED DESCRIPTION OF THE INVENTION

Figure 1A:
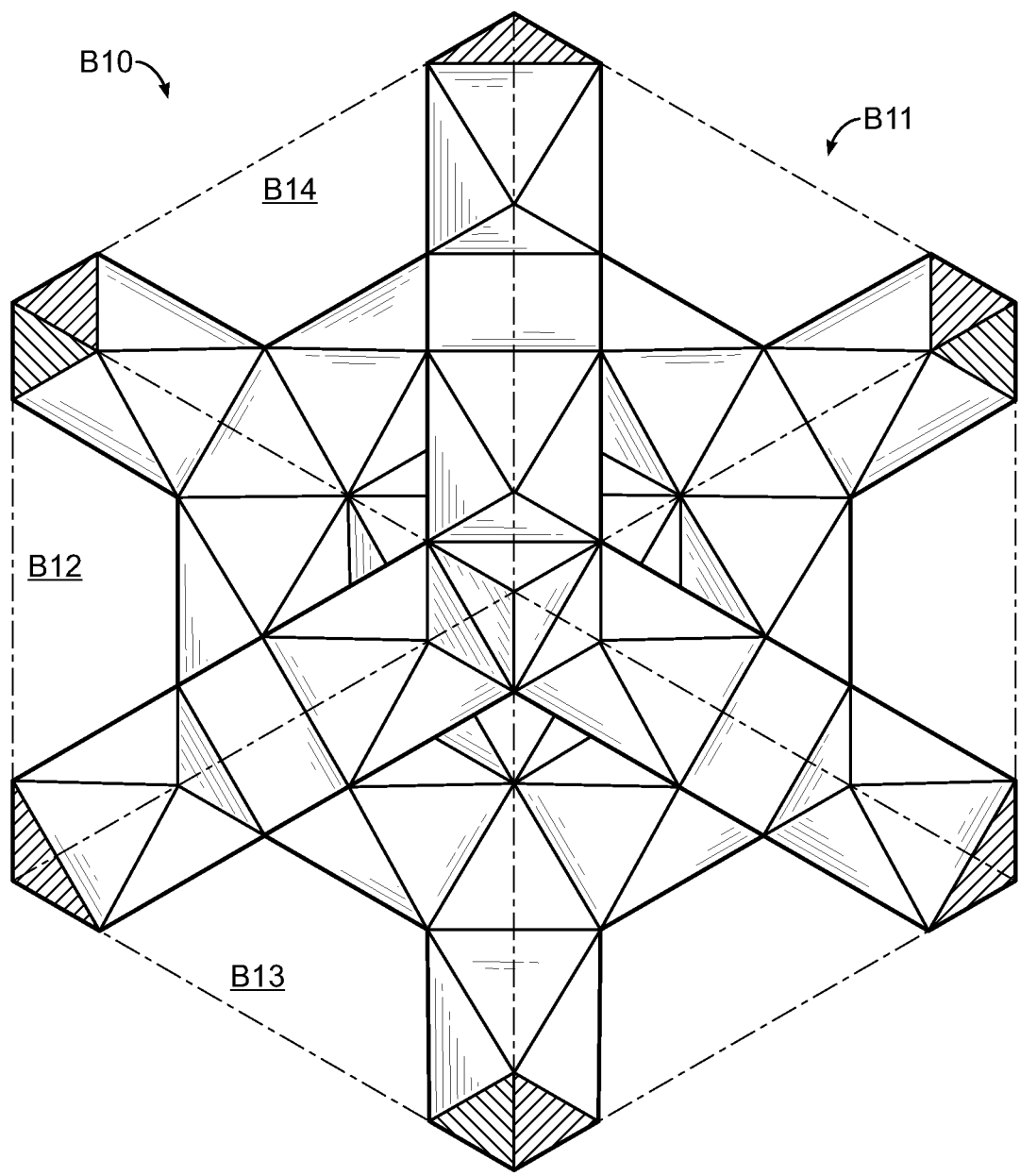
FIG. 1A is an isometric view of a single modified rhombic dodecahedron unit cell containing a full modified rhombic dodecahedron structure along with radial struts that comprise portions of adjacent unit cells.

In many situations, it is desirable to use an implant that is capable of bone attachment or osteointegration over time. It is also desirable in many situations to use an implant that is capable of attachment or integration with living tissue. Examples of implants where attachment to bone or osteointegration is beneficial include, but are not limited to, cervical, lumbar, and thoracic interbody fusion implants, vertebral body replacements, osteotomy wedges, dental implants, bone stems, acetabular cups, cranio-facial plating, bone replacement and fracture plating. In many applications, it is also desirable to stress new bone growth to increase its strength. According to Wolff s law, bone will adapt to stresses placed on it so that bone under stress will grow stronger and bone that isn't stressed will become weaker.

In some aspects, the systems and methods described herein can be directed toward implants that are configured for osteointegration and stimulating adequately stressed new bone growth. Many of the exemplary implants of the present invention are particularly useful for use in situations where it is desirable to have strong bone attachment and/or bone growth throughout the body of an implant. Whether bone growth is desired only for attachment or throughout an implant, the present invention incorporates a unique lattice structure that can provide mechanical spacing, a scaffold to support new bone growth and a modulus of elasticity that allows new bone growth to be loaded with physiological forces. As a result, the present invention provides implants that grow stronger and healthier bone for more secure attachment and/or for a stronger bone after the implant osteointegrates.

The exemplary embodiments of the invention presented can be comprised, in whole or in part, of a lattice. A lattice, as used herein, refers to a three-dimensional material with one or more interconnected openings that allow a fluid to communicate from one location to another location through an opening. A three-dimensional material refers to a material that fills a three-dimensional space (i.e. has height, width and length). Lattices can be constructed by many means, including repeating various geometric shapes or repeating random shapes to accomplish a material with interconnected openings. An opening in a lattice is any area within the bounds of the three-dimensional material that is devoid of that material. Therefore, within the three-dimensional boundaries of a lattice, there is a volume of material and a volume that is devoid of that material.

The material that provides the structure of the lattice is referred to as the primary material. The structure of a lattice does not need to provide structural support for any purpose, but rather refers to the configuration of the openings and interconnections that comprise the lattice. An opening in a lattice may be empty, filled with a gaseous fluid, filled with a liquid fluid, filled with a solid or partially filled with a fluid and/or solid. Interconnections, with respect to openings, refer to areas devoid of the primary material and that link at least two locations together. Interconnections may be configured to allow a fluid to pass from one location to another location.

A lattice can be defined by its volumetric density, meaning the ratio between the volume of the primary material and the volume of voids presented as a percentage for a given three-dimensional material. The volume of voids is the difference between the volume of the bounds of the three-dimensional material and the volume of the primary material. The volume of voids can comprise of the volume of the openings, the volume of the interconnections and/or the volume of another material present. For example, a lattice with a 30% volumetric density would be comprised of 30% primary material by volume and 70% voids by volume over a certain volume. A lattice with a 90% volumetric density would be comprised of 90% primary material by volume and 10% voids by volume over a certain volume. In three-dimensional materials with a volumetric density of less than 50%, the volume of the primary material is less than the volume of voids. While the volumetric density refers to the volume of voids, the voids do not need to remain void and can be filled, in whole or in part, with a fluid or solid prior to, during or after implantation.

Lattices comprised of repeating geometric patterns can be described using the characteristics of a repeating unit cell. A unit cell in a repeating geometric lattice is a three-dimensional shape capable of being repeated to form a lattice. A repeating unit cell can refer to multiple identical unit cells that are repeated over a lattice structure or a pattern through all or a portion of a lattice structure. Each unit cell is comprised of a certain volume of primary material and a certain void volume, or in other words, a spot volumetric density. The spot volumetric density may cover as few as a partial unit cell or a plurality of unit cells. In many situations, the spot volumetric density will be consistent with the material's volumetric density, but there are situations where it could be desirable to locally increase or decrease the spot volumetric density.

Unit cells can be constructed in numerous volumetric shapes containing various types of structures. Unit cells can be bound by a defined volume of space to constrict the size of the lattice structure or other type of structure within the unit cell. In some embodiments, unit cells can be bound by volumetric shapes, including but not limited to, a cubic volume, a cuboid volume, a hexahedron volume or an amorphous volume. The unit cell volume of space can be defined based on a number of faces that meet at corners. In examples where the unit cell volume is a cubic, cuboid or hexahedron volume, the unit cell volume can have six faces and eight corners, where the corners are defined by the location where three faces meet. Unit cells may be interconnected in some or all areas, not interconnected in some or all areas, of a uniform size in some or all areas or of a nonuniform size in some or all areas. In some embodiments disclosed herein that use a repeating geometric pattern, the unit cells can be defined by a number of struts defining the edges of the unit cell and joined at nodes about the unit cell. Unit cells so defined can share certain struts among more than one unit cell, so that two adjacent unit cells may share a common planar wall defined by struts common to both cells. In some embodiments disclosed herein that use a repeating geometric pattern, the unit cells can be defined by a node and a number of struts extending radially from that node.

While the present application uses volumetric density to describe exemplary embodiments, it is also possible to describe them using other metrics, including but not limited to cell size, strut size or stiffness. Cell size may be defined using multiple methods, including but not limited to cell diameter, cell width, cell height and cell volume. Strut size may be defined using multiple methods, including but not limited to strut length and strut diameter.

Repeating geometric patterns are beneficial for use in lattice structures contained in implants because they can provide predictable characteristics. Many repeating geometric shapes may be used as the unit cell of a lattice, including but are not limited to, rhombic dodecahedron, diamond, dodecahedron, square, pentagonal, hexagonal, octagonal, sctet struts, trunic octa, diagonal struts, other known geometric structures, and rounded, reinforced, weakened, or simplified versions of each geometry.

Lattices may also be included in implants as a structural component or a nonstructural component. Lattices used in structural applications may be referred to herein as structural lattices, load-bearing lattices or stressed lattices. In some instances, structural lattices, load-bearing lattices or stressed lattices may be simply referred to as a lattice. Repeating geometric shaped unit cells, particularly the rhombic dodecahedron, are well suited, in theory, for use in structural lattices because of their strength to weight ratio. To increase the actual strength and fatigue resistance of a rhombic dodecahedron lattice, the present invention, in some embodiments, includes a modified strut comprised of triangular segments, rather than using a strut with a rectangular or circular cross section. Some embodiments herein also modify the angles defining the rhombic faces of a rhombic dodecahedron to change the lattice's elastic modulus and fatigue resistance. The use of triangular segments provides a lattice with highly predictable printed properties that approach the theoretical strength values for a rhombic dodecahedron lattice.

In structural lattice applications, the strength and elastic modulus of the lattice can be approximated by the volumetric density. When the volumetric density increases, the strength and the elastic modulus increases. Compared to other porous structures, the lattice of the present invention has a higher strength and elastic modulus for a given volumetric density because of its ability to use the high strength to weight benefits of a rhombic dodecahedron, modified rhombic dodecahedron or radial dodeca-rhombus unit cell.

The term "elastic modulus," as used herein, can refer to either the elastic modulus of a material or the effective elastic modulus of a volume of material. An elastic modulus quantifies a material or volume of material's resistance to elastic deformation in response to a stress. A volume of material can have an elastic modulus of the material itself and an effective elastic modulus of the entire volume of material. An effective elastic modulus can be determined by compressing the volume of material and treating it as a homogenous material for the purposes of calculating the effective elastic modulus. When the term "elastic modulus" is used herein, it can refer to both or either of the elastic modulus of a material or the effective elastic modulus of a volume of material.

When configured to provide support for bone or tissue growth, a lattice may be referred to as a scaffold. Lattices can be configured to support bone or tissue growth by controlling the size of the openings and interconnections disposed within the three-dimensional material. A scaffold, if used on the surface of an implant, may provide an osteointegration surface that allows adjacent bone to attach to the implant. A scaffold may also be configured to provide a path that allows bone to grow further than a mere surface attachment. Scaffolds intended for surface attachment are referred to herein as surface scaffolds. A surface scaffold may be one or more unit cells deep, but does not extend throughout the volume of an implant. Scaffolds intended to support in-growth beyond mere surface attachment are referred to herein as bulk scaffolds. Scaffolds may also be included in implants as a structural component or a nonstructural component. Scaffolds used in structural applications may be referred to herein as structural scaffolds, load-bearing scaffolds or stressed scaffolds. In some instances, structural scaffolds, load-bearing scaffolds or stressed scaffolds may be simply referred to as a scaffold. In some instances, the use of the term scaffold may refer to a material configured to provide support for bone or tissue growth, where the material is not a lattice.

The scaffolds described herein can be used to promote the attachment or in-growth of various types of tissue found in living beings. As noted earlier, some embodiments of the scaffold are configured to promote bone attachment and in-growth. The scaffolds can also be configured to promote attachment of in-growth of other areas of tissue, such as fibrous tissue. In some embodiments, the scaffold can be configured to promote the attachment or in-growth of multiple types of tissue. Some embodiments of the scaffolds are configured to be implanted near or abutting living tissue. Near living tissue includes situations where other layers, materials or coatings are located between a scaffold and any living tissue.

In some embodiments, the present invention uses bulk scaffolds with openings and interconnections that are larger than those known in the art. Osteons can range in diameter from about 100 µm and it is theorized that a bundle of osteons would provide the strongest form of new bone growth. Bone is considered fully solid when it has a diameter of greater than 3 mm so it is theorized that a bundle of osteons with a diameter equaling approximately half of that value would provide significant strength when grown within a scaffold. It is also theorized that osteons may grow in irregular shapes so that the cross-sectional area of an osteon could predict its strength. A cylindrical osteon growth with a 3 mm diameter has a cross-sectional area of approximately 7 square mm and a cylindrical osteon with a 1.5 mm diameter has a cross-sectional area of 1.8 square mm. It is theorized that an osteon of an irregular shape with a cross-sectional area of at least 1.8 square millimeters could provide a significant strength advantage when grown in a scaffold.

Most skilled in the art would indicate that pores or openings with a diameter or width between 300 μm to 900 μm, with a pore side of 600 μm being ideal, provide the best scaffold for bone growth. Instead, some embodiments of the present invention include openings and interconnections with a diameter or width on the order of 1.0 to 15.0 times the known range, with the known range being 300 μm to 900 μm, resulting in openings from 0.07 mm$^2$ up to 145 mm$^2$ cross sectional area for bone growth. In some examples, pores or openings with a diameter or width between and including 100 μm to 300 μm could be beneficial. Some examples include openings and interconnections with a diameter on the order of 1.0 to 5.0 times the known range. It has been at least theorized that the use of much larger openings and interconnections than those known in the art will allow full osteons and solid bone tissue to form throughout the bulk scaffold, allowing the vascularization of new, loadable bone growth. In some examples, these pores may be 3 mm in diameter or approximately 7 mm$^2$ in cross sectional area. In other examples, the pores are approximately 1.5 mm in diameter or approximately 1.75 mm$^2$ in cross sectional area. The use of only the smaller diameter openings and interconnections known in the art are theorized to limit the penetration of new bone growth into a bulk scaffold because the smaller diameter openings restrict the ability of vascularization throughout the bulk scaffold.

A related structure to a lattice is a closed cell material. A closed cell material is similar to a lattice, in that it has openings contained within the bounds of a three-dimensional material, however, closed cell materials generally lack interconnections between locations through openings or other pores. A closed cell structure may be accomplished using multiple methods, including the filling of certain cells or through the use of solid walls between the struts of unit cells. A closed cell structure can also be referred to as a cellular structure. It is possible to have a material that is a lattice in one portion and a closed cell material in another. It is also possible to have a closed cell material that is a lattice with respect to only certain interconnections between openings or vice versa. While the focus of the present disclosure is on lattices, the structures and methods disclosed herein can be easily adapted for use on closed cell structures within the inventive concept.

The lattice used in the present invention can be produced from a range of materials and processes. When used as a scaffold for bone growth, it is desirable for the lattice to be made of a biocompatible material that allows for bone attachment, either to the material directly or through the application of a bioactive surface treatment. In one example, the scaffold is comprised of an implantable metal. Implantable metals include, but are not limited to, zirconium, stainless steel (316 & 316L), tantalum, nitinol, cobalt chromium alloys, titanium and tungsten, and alloys thereof. Scaffolds comprised of an implantable metal may be produced using an additive metal fabrication or 3D printing process. Appropriate production processes include, but are not limited to, direct metal laser sintering, selective laser sintering, selective laser melting, electron beam melting, laminated object manufacturing and directed energy deposition.

In another example, the lattice of the present invention is comprised of an implantable metal with a bioactive coating. Bioactive coatings include, but are not limited to, coatings to accelerate bone growth, anti-thrombogenic coatings, anti-microbial coatings, hydrophobic or hydrophilic coatings, and hemophobic, superhemophobic, or hemophilic coatings. Coatings that accelerate bone growth include, but are not limited to, calcium phosphate, hydroxyapatite ("HA"), silicate glass, stem cell derivatives, bone morphogenic proteins, titanium plasma spray, titanium beads and titanium mesh. Anti-thrombogenic coatings include, but are not limited to, low molecular weight fluoro-oligomers. Anti-microbial coatings include, but are not limited to, silver, organosilane compounds, iodine and silicon-nitride. Superhemophobic coatings include fluorinated nanotubes.

In another example, the lattice is made from a titanium alloy with an optional bioactive coating. In particular, Ti6Al4V ELI wrought (American Society for Testing and Materials ("ASTM") F136) is a particularly well-suited titanium alloy for scaffolds. While Ti6Al4V ELI wrought is the industry standard titanium alloy used for medical purposes, other titanium alloys, including but not limited to, unalloyed titanium (ASTM F67), Ti6Al4V standard grade (ASTM F1472), Ti6Al7Nb wrought (ASTM 1295), Ti5Al2.5Fe wrought (British Standards Association/International Standard Organization Part 10), CP and Ti6Al4V standard grade powders (ASTM F1580), Ti13Nb13Zr wrought (ASTM F1713), the lower modulus Ti-24Nb-4Zr-8Sn and Ti12Mo6Zr2Fe wrought (ASTM F1813) can be appropriate for various embodiments of the present invention.

Titanium alloys are an appropriate material for scaffolds because they are biocompatible and allow for bone attachment. Various surface treatments can be done to titanium alloys to increase or decrease the level of bone attachment. Bone will attach to even polished titanium, but titanium with a surface texture allows for greater bone attachment. Methods of increasing bone attachment to titanium may be produced through a forging or milling process, sandblasting, acid etching, and the use of a bioactive coating. Titanium parts produced with an additive metal fabrication or 3D printing process, such as direct metal laser sintering, can be treated with an acid bath to reduce surface stress risers, normalize surface topography, and improve surface oxide layer, while maintaining surface roughness and porosity to promote bone attachment.

Additionally, Titanium or other alloys may be treated with heparin, heparin sulfate (HS), glycosaminoglycans (GAG), chondroitin-4-sulphate (C4S), chondroitin-6-sulphate (C6S), hyaluronan (HY), and other proteoglycans with or without an aqueous calcium solution. Such treatment may occur while the material is in its pre-manufacturing form (often powder) or subsequent to manufacture of the structure.

While a range of structures, materials, surface treatments and coatings have been described, it is believed that a lattice using a repeating modified rhombic dodecahedron (hereinafter "MRDD") unit cell can present a preferable combination of stiffness, strength, fatigue resistance, and conditions for bone ingrowth. In some embodiments, the repeating MRDD lattice is comprised of titanium or a titanium alloy. A generic rhombic dodecahedron (hereinafter "RDD"), by definition, has twelve sides in the shape of rhombuses. When repeated in a lattice, an RDD unit cell is comprised of 24 struts that meet at 14 vertices. The 24 struts define the 12 planar faces of the structure and disposed at the center of each planar face is an opening, or interconnection, allowing communication from inside the unit cell to outside the unit cell.

Figure 1B:
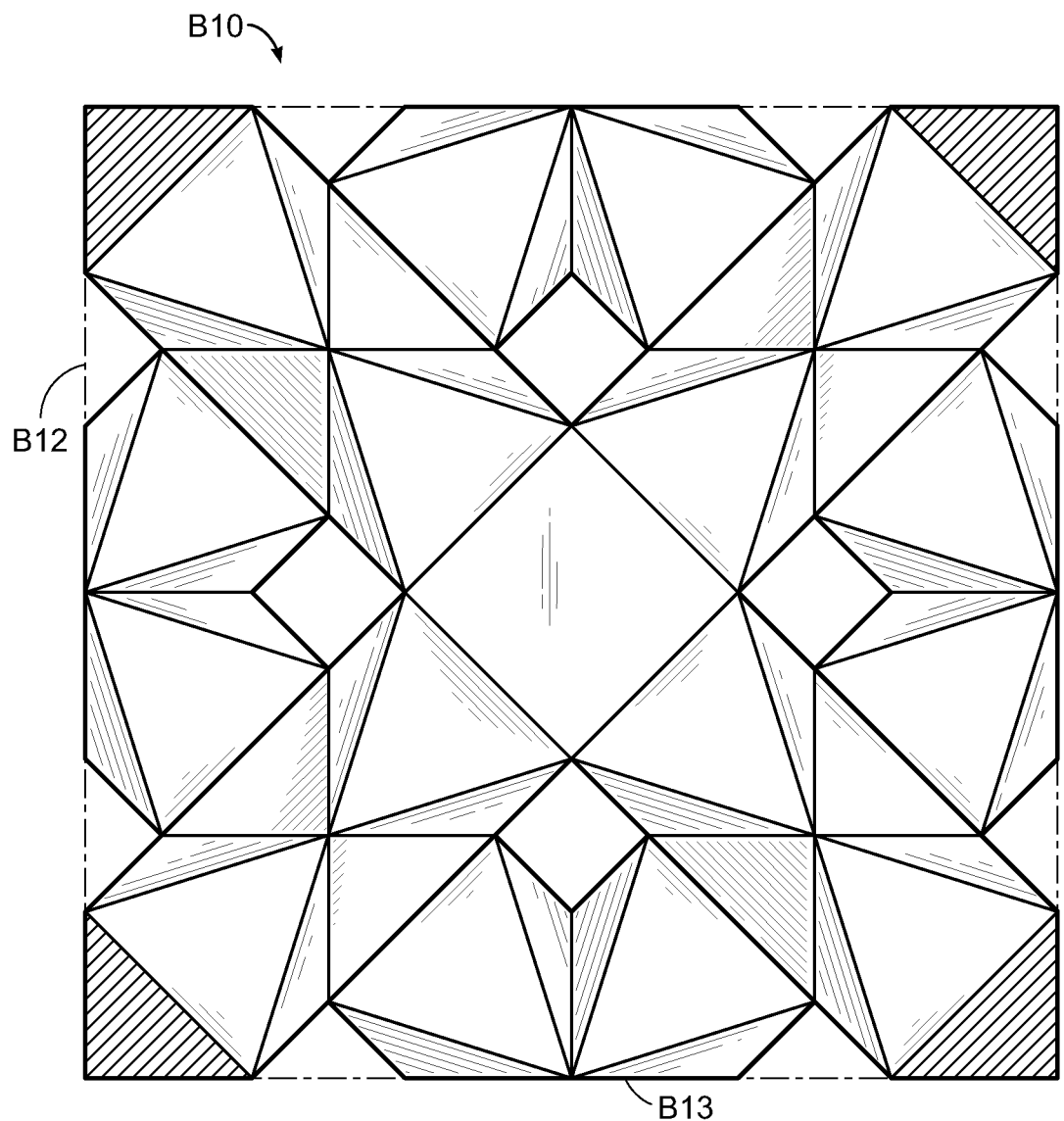
FIG. 1B is a side view of a single modified rhombic dodecahedron unit cell showing the configuration of interconnections when viewed from a lateral direction.

An example of the MRDD unit cell B10 used in the present invention is shown in FIGS. 1A-1E. In FIG. 1A is an isometric view of a single MRDD unit cell B10 containing a full MRDD structure along with radial struts that comprise portions of adjacent unit cells. In FIG. 1B is a side view of a single MRDD unit cell B10 showing the configuration of interconnections when viewed from a lateral direction. A top or bottom view of the MRDD unit cell B10 would be substantially the same as the side view depicted in FIG. 1B. The MRDD unit cell B10 differs in both structural characteristics and method of design from generic RDD shapes. A generic RDD is comprised of 12 faces where each face is an identical rhombus with an acute angle of 70.5 degrees and an obtuse angle of 109.5 degrees. The shape of the rhombus faces in a generic RDD do not change if the size of the unit cell or the diameter of the struts are changed because the struts are indexed based on their axis and each pass through the center of the 14 nodes or vertices.

In some embodiments of the MRDD, each node is contained within a fixed volume that defines its bounds and provides a fixed point in space for the distal ends of the struts. The fixed volume containing the MRDD or a sub-unit cell of the MRDD can be various shapes, including but not limited to, a cubic, cuboid, hexahedron or amorphous volume. Some examples use a fixed volume with six faces and eight corners defined by locations where three faces meet. The orientation of the struts can be based on the center of a node face at its proximate end and the nearest corner of the volume to that node face on its distal end. Each node is preferably an octahedron, more specifically a square bipyramid (i.e. a pyramid and inverted pyramid joined on a horizontal plane). Each node, when centrally located in a cuboid volume, more preferably comprises a square plane parallel to a face of the cuboid volume, six vertices and is oriented so that each of the six vertices are positioned at their closest possible location to each of the six faces of the cuboid volume. Centrally located, with regards to the node's location within a volume refers to positioning the node at a location substantially equidistant from opposing walls of the volume. In some embodiments, the node can have a volumetric density of 100 percent and in other embodiments, the node can have a volumetric density of less than 100 percent. Each face of the square bipyramid node can be triangular and each face can provide a connection point for a strut.

The struts can also be octahedrons, comprising an elongate portion of six substantially similar elongate faces and two end faces. The elongate faces can be isosceles triangles with a first internal angle, angle A, and a second internal angle, angle B, where angle B is greater than angle A. The end faces can be substantially similar isosceles triangles to one another with a first internal angle, angle C, and a second internal angle, angle D, where angle D is greater than angle C. Preferably, angle C is greater than angle A.

The strut direction of each strut is a line or vector defining the orientation of a strut and it can be orthogonal or non-orthogonal relative to the planar surface of each node face. In the MRDD and radial dodeca-rhombus structures disclosed herein, the strut direction can be determined using a line extending between the center of the strut end faces, the center of mass along the strut or an external edge or face of the elongate portion of the strut. When defining a strut direction using a line extending between the center of the strut end faces, the line is generally parallel to the bottom face or edge of the strut. When defining a strut direction using a line extending along the center of mass of the strut, the line can be nonparallel to the bottom face or edge of the strut. The octahedron nodes of the MRDD can be scaled to increase or decrease volumetric density by changing the origin point and size of the struts. The distal ends of the struts, however, are locked at the fixed volume corners formed about each node so that their angle relative to each node face changes as the volumetric density changes. Even as the volumetric density of an MRDD unit cell changes, the dimensions of the fixed volume formed about each node does not change. In FIG. A1, dashed lines are drawn between the corners of the MRDD unit cell B10 to show the cube B11 that defines its bounds. In the MRDD unit cell in FIG. A1, the height B12, width B13 and depth B14 of the unit cell are substantially the same, making the area defined by B11 a cube.

In some embodiments, the strut direction of a strut can intersect the center of the node and the corner of the cuboid volume nearest to the node face where the strut is fixed. In some embodiments, the strut direction of a strut can intersect just the corner of the cuboid volume nearest to the node face where the strut is fixed. In some embodiments, a reference plane defined by a cuboid or hexahedron face is used to describe the strut direction of a strut. When the strut direction of a strut is defined based on a reference plane, it can be between 0 degrees and 90 degrees from the reference plane. When the strut direction of a strut is defined based on a reference plane, it is preferably eight degrees to 30 degrees from the reference plane.

By indexing the strut orientation to a variable node face on one end and a fixed point on its distal end, the resulting MRDD unit cell can allow rhombus shaped faces with a smaller acute angle and larger obtuse angle than a generic RDD. The rhombus shaped faces of the MRDD can have two substantially similar opposing acute angles and two substantially similar opposing obtuse angles. In some embodiments, the acute angles are less than 70.5 degrees and the obtuse angles are greater than 109.5 degrees. In some embodiments, the acute angles are between 0 degrees and 55 degrees and the obtuse angles are between 125 degrees and 180 degrees. In some embodiments, the acute angles are between 8 degrees and 60 degrees and the obtuse angles are between 120 degrees and 172 degrees. The reduction in the acute angles increases fatigue resistance for loads oriented across the obtuse angle corner to far obtuse angle corner. The reduction in the acute angles and increase in obtuse angles also orients the struts to increase the MRDD's strength in shear and increases the fatigue resistance. By changing the rhombus corner angles from a generic RDD, shear loads pass substantially in the axial direction of some struts, increasing the shear strength. Changing the rhombus corner angles from a generic RDD also reduces overall deflection caused by compressive loads, increasing the fatigue strength by resisting deflection under load.

Figure 1C:
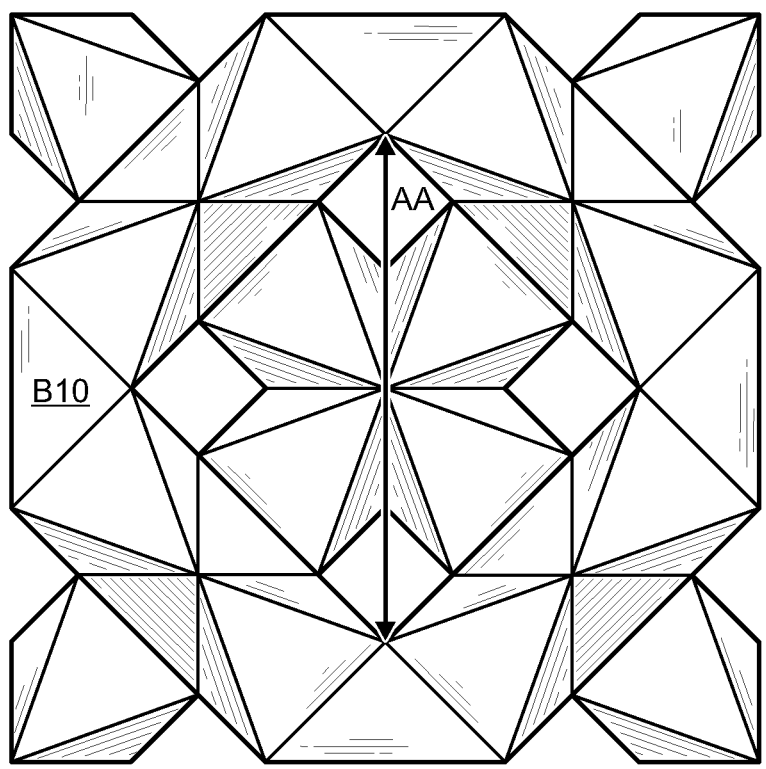
FIG. 1C is a side view of a single modified rhombic dodecahedron unit cell where the central void is being measured using the longest dimension method.
Figure 1D:
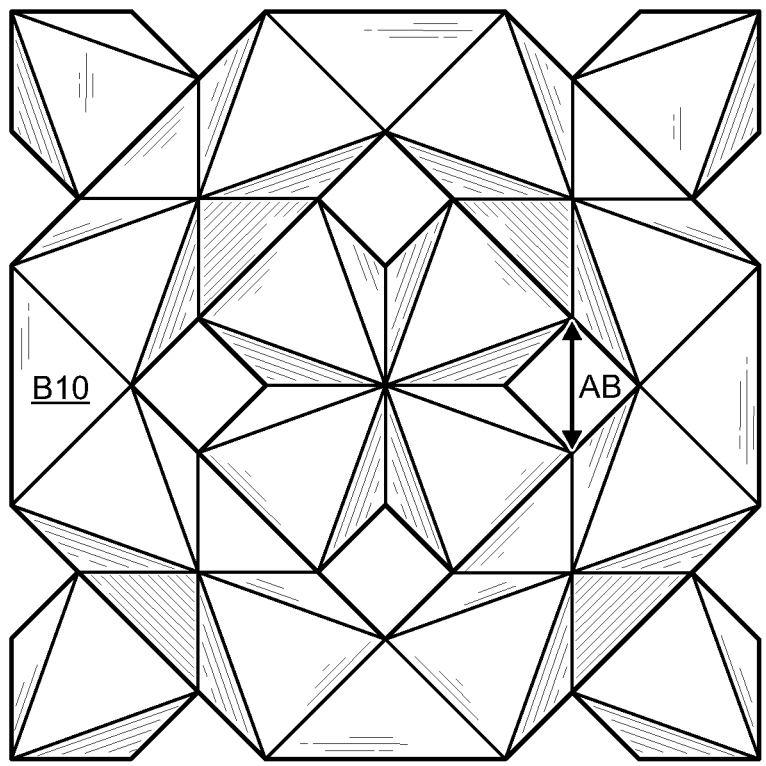
FIG. 1D is a side view of a single modified rhombic dodecahedron unit cell where an interconnection is being measured using the longest dimension method.

When placed towards the center of a lattice structure, the 12 interconnections of a unit cell connect to 12 different adjacent unit cells, providing continuous paths through the lattice. The size of the central void and interconnections in the MRDD may be defined using the longest dimension method as described herein. Using the longest dimension method, the central void can be defined by taking a measurement of the longest dimension as demonstrated in FIG. 1C. In FIG. 1C, the longest dimension is labeled as distance AA. The distance AA can be taken in the vertical or horizontal directions (where the directions reference the directions on the page) and would be substantially the same in this example. The interconnections may be defined by their longest measurement when viewed from a side, top or bottom of a unit cell. In FIG. 1D, the longest dimension is labeled as distance AB. The distance AB can be taken in the vertical or horizontal directions (where the directions reference the directions on the page). The view in FIG. 1D is a lateral view, however, in this example the unit cell will appear substantially the same when viewed from the top or bottom.

Figure 1E:
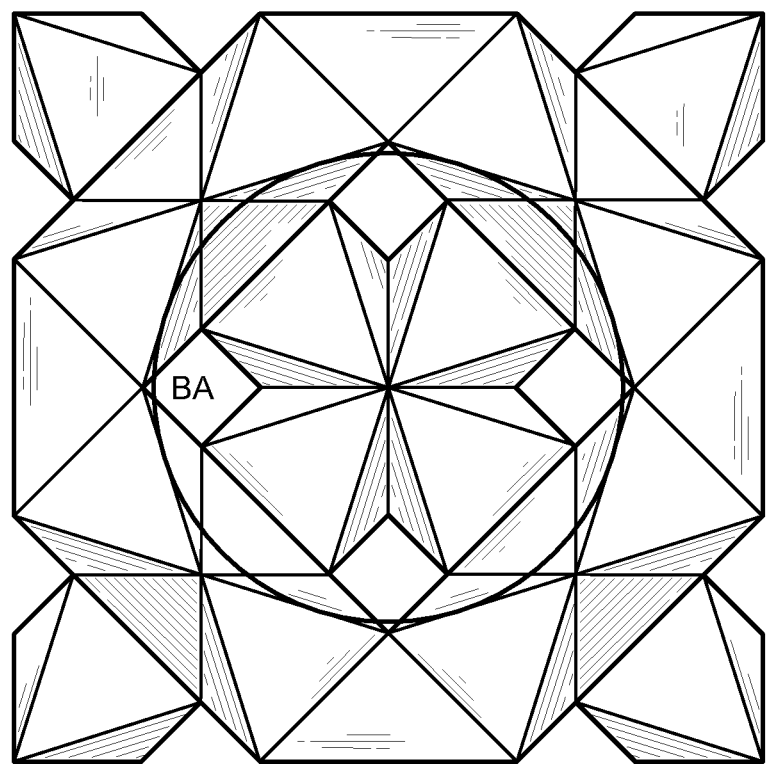
FIG. 1E is a side view of the central void of a modified rhombic dodecahedron unit cell being measured with the largest sphere method.
Figure 1F:
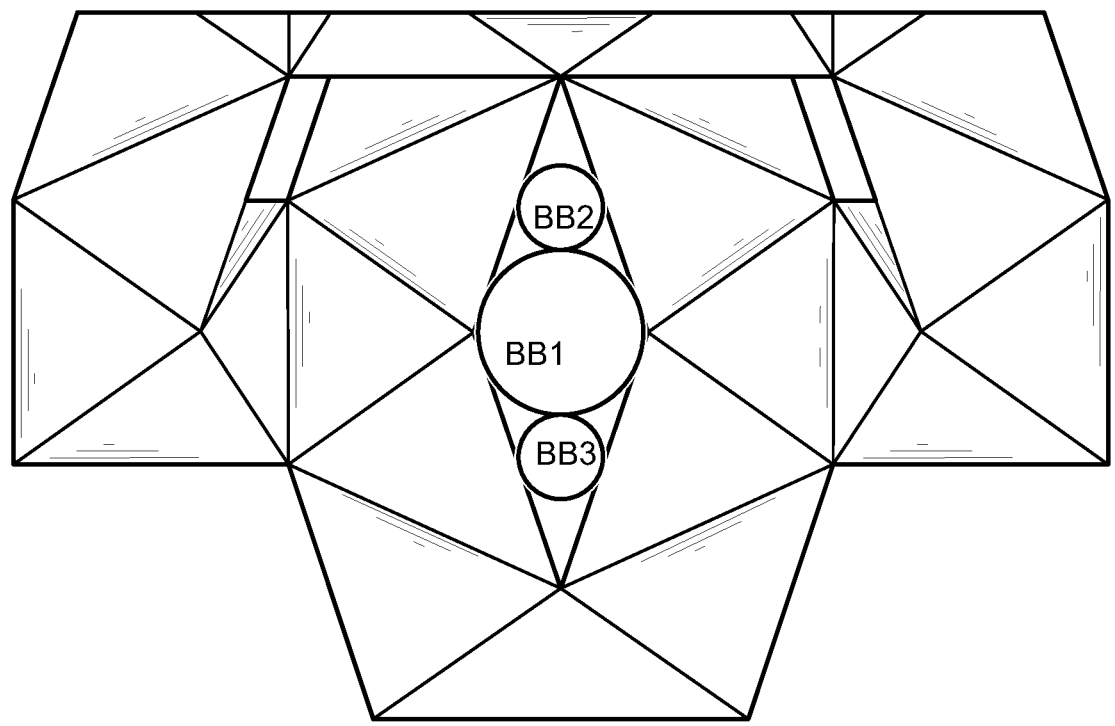
FIG. 1F is a view from a direction normal to the planar direction of an interconnection being measured with the largest sphere method.

The size of the central void and interconnections can alternatively be defined by the largest sphere method as described herein. Using the largest sphere method, the central void can be defined by the diameter of the largest sphere that can fit within the central void without intersecting the struts. In FIG. 1E is an example of the largest sphere method being used to define the size of a central void with a sphere with a diameter of BA. The interconnections are generally rhombus shaped and their size can alternatively be defined by the size of the length and width of three circles drawn within the opening. Drawn within the plane defining a side, a first circle BB1 is drawn at the center of the opening so that it is the largest diameter circle that can fit without intersecting the struts. A second circle BB2 and third circle BB3 is them drawn so that they are tangential to the first circle BB1 and the largest diameter circles that can fit without intersecting the struts. The diameter of the first circle BB1 is the width of the interconnection and the sum of the diameters of all three circles BB1, BB2 & BB3 represents the length of the interconnection. Using this method of measurement removes the acute corners of the rhombus shaped opening from the size determination. In some instances, it is beneficial to remove the acute corners of the rhombus shaped opening from the calculated size of the interconnections because of the limitations of additive manufacturing processes. For example, if an SLS machine has a resolution of 12 µm where the accuracy is within 5 µm, it is possible that the acute corner could be rounded by the SLS machine, making it unavailable for bone ingrowth. When designing lattices for manufacture on less precise additive process equipment, it can be helpful to use this measuring system to better approximate the size of the interconnections.

Using the alternative measuring method, in some examples, the width of the interconnections is approximately 600 µm and the length of the interconnections is approximately 300 µm. The use of a 600 µm length and 300 µm width provides an opening within the known pore sizes for bone growth and provides a surface area of roughly 1.8 square millimeters, allowing high strength bone growth to form. Alternative embodiments may contain interconnections with a cross sectional area of 1.0 to 15.0 times the cross-sectional area of a pore with a diameter of 300 µm. Other embodiments may contain interconnections with a cross sectional area of 1.0 to 15.0 times the cross-sectional area of a pore with a diameter of 900 µm.

The MRDD unit cell also has the advantage of providing at least two sets of substantially homogenous pore or opening sizes in a lattice structure. In some embodiments, a first set of pores have a width of about 200 µm to 900 µm and a second set of pores have a width of about 1 to 15 times the width of the first set of pores. In some embodiments, a first set of pores can be configured to promote the growth of osteoblasts and a second set of pores can be configured to promote the growth of osteons. Pores sized to promote osteoblast growth can have a width of between and including about 100 µm to 900 µm. In some embodiments, pores sized to promote osteoblast growth can have a width that exceeds 900 µm. Pores sized to promote the growth of osteons can have a width of between and including about 100 µm to 13.5 mm. In some embodiments, pores sized to promote osteon growth can have a width that exceeds 13.5 mm.

In some embodiments, it is beneficial to include a number of substantially homogenous larger pores and a number of substantially homogenous smaller pores, where the number of larger pores is selected based on a ratio relative to the number of smaller pores. For example, some embodiments have one large pore for every one to 25 small pores in the lattice structure. Some embodiments preferably have one large pore for every eight to 12 smaller pores. In some embodiments, the number of larger and smaller pores can be selected based on a percentage of the total number of pores in a lattice structure. For example, some embodiments can include larger pores for four percent to 50 percent of the total number of pores and smaller pores for 50 percent to 96 percent of the total number of pores. More preferably, some embodiments can include larger pores for about eight percent to 13 percent of the total number of pores and smaller pores for about 87 percent to 92 percent of the total number of pores. It is believed that a lattice constructed with sets of substantially homogenous pores of the disclosed two sizes provides a lattice structure that simultaneously promotes osteoblast and osteon growth.

The MRDD unit cell may also be defined by the size of the interconnections when viewed from a side, top or bottom of a unit cell. The MRDD unit cell has the same appearance when viewed from a side, top or bottom, making the measurement in a side view representative of the others. When viewed from the side, as in FIG. 1D, an MRDD unit cell displays four distinct diamond shaped interconnections with substantially right angles. The area of each interconnection is smaller when viewed in the lateral direction than from a direction normal to the planar direction of each interconnection, but the area when viewed in the lateral direction can represent the area available for bone to grow in that direction. In some embodiments, it may be desirable to index the properties of the unit cell and lattice based on the area of the interconnections when viewed from the top, bottom or lateral directions.

In some embodiments of the lattice structures disclosed herein, the central void is larger than the length or width of the interconnections. Because the size of each interconnection can be substantially the same in a repeating MRDD structure, the resulting lattice can be comprised of openings of at least two discrete sizes. In some embodiments, it is preferable for the diameter of the central void to be approximately two times the length of the interconnections. In some embodiments, it is preferable for the diameter of the central void to be approximately four times the width of the interconnections.

In some embodiments, the ratio between the diameter of the central void and the length or width of the interconnections can be changed to create a structural lattice of a particular strength. In these embodiments, there is a correlation where the ratio between the central void diameter and the length or width of the interconnections increases as the strength of the structural lattice increases.

Figure 1G:
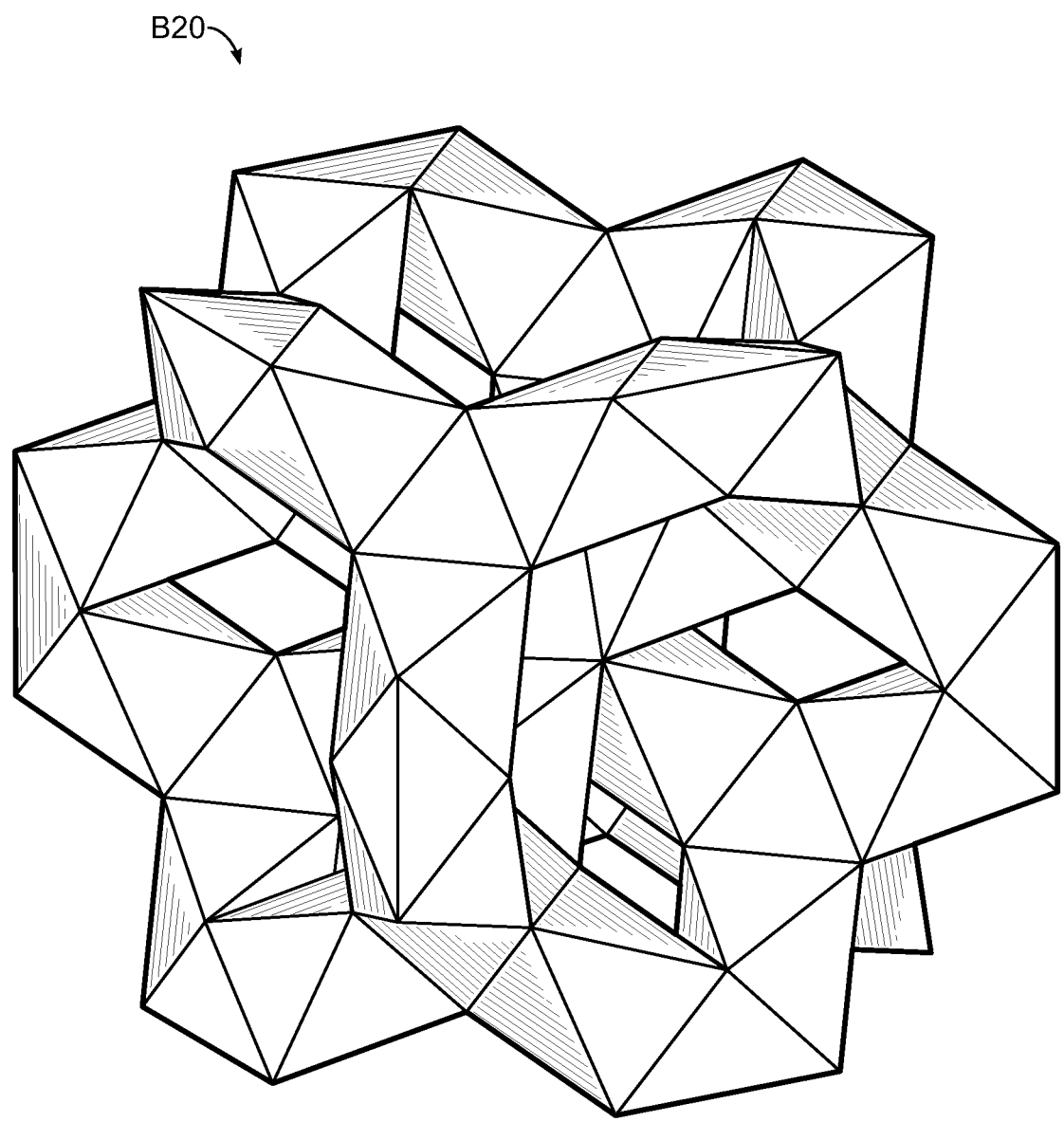
FIG. 1G is an isometric view of a single radial dodeca-rhombus unit cell.
Figure 1H:
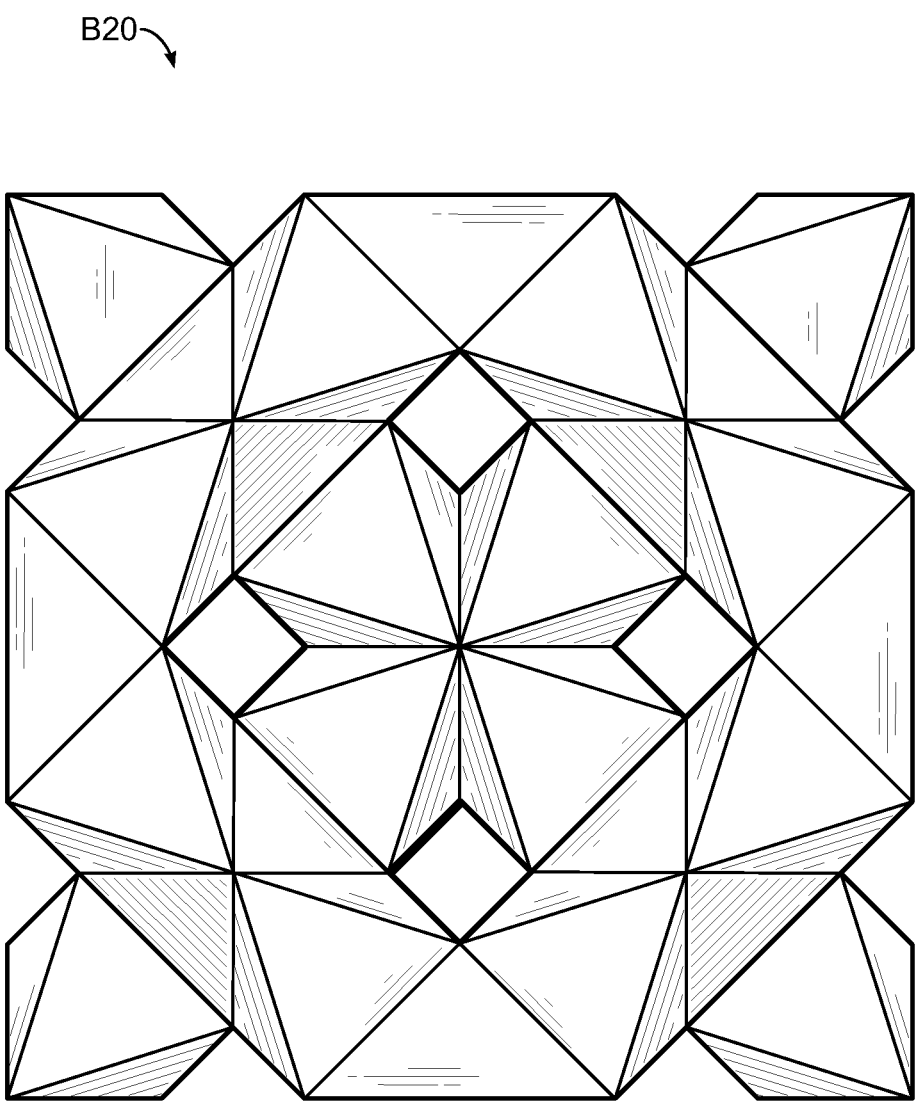
FIG. 1H is a side view of a single radial dodeca-rhombus unit cell.

It is also believed that a lattice using a repeating radial dodeca-rhombus (hereinafter "RDDR") unit cell can present a preferable combination of stiffness, strength, fatigue resistance, and conditions for bone ingrowth. In some embodiments, the repeating RDDR lattice is comprised of titanium or a titanium alloy. In FIG. 1G is an isometric view of a single RDDR unit cell B20 containing a full RDDR structure. In FIG. 1H is a side view of a single RDDR unit cell B20 showing the configuration of interconnections when viewed from a lateral direction. A top or bottom view of the RDDR unit cell B20 would be substantially the same as the side view depicted in FIG. 1H.

As used herein, an RDDR unit cell B20 is a three-dimensional shape comprised of a central node with radial struts and mirrored struts thereof forming twelve rhombus shaped structures. The node is preferably an octahedron, more specifically a square bipyramid (i.e. a pyramid and inverted pyramid joined on a horizontal plane). Each face of the node is preferably triangular and fixed to each face is a strut comprised of six triangular facets and two end faces. The central axis of each strut can be orthogonal or non-orthogonal relative to the planar surface of each node face. The central axis may follow the centroid of the strut. The RDDR is also characterized by a central node with one strut attached to each face, resulting in a square bipyramid node with eight struts attached.

Figure 1I:
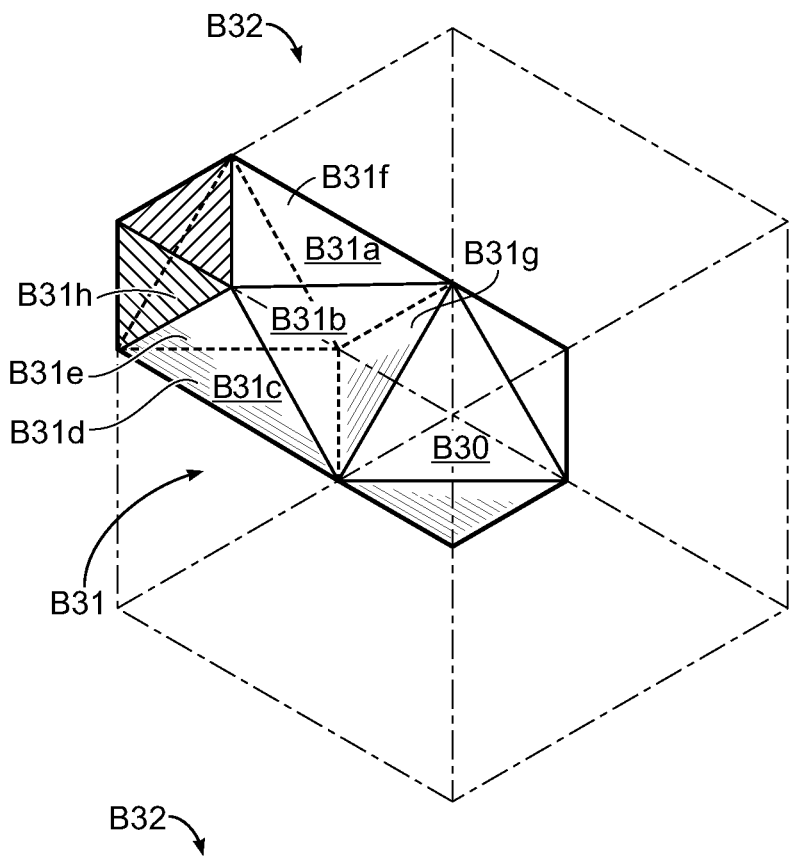
FIG. 1I is an isometric view of an example of a single node and single strut combination that could be used in a radial dodeca-rhombus unit cell.

Examples of node and strut combinations are shown in FIGS. 1I-1M. In FIG. 1I is an isometric view of a single node B30 with a single strut B31 attached. The node B30 is a square bipyramid oriented so that two peaks face the top and bottom of a volume B32 defining the bounds of the node B30 and any attached strut(s) B31. The node B30 is oriented so that the horizontal corners are positioned at their closest point to the lateral sides of the volume B32. The strut B31 extends from a node B30 face to the corner of the volume B32 defining the bounds of the node and attached struts. In FIG. 1I, the central axis of the strut is 45 degrees above the horizontal plane where the node's planar face is 45 degrees above a horizontal plane.

FIG. 1I also details an octahedron strut B31, where dashed lines show hidden edges of the strut. The strut B31 is an octahedron with an elongate portion of six substantially similar elongate faces and two end faces. The elongate faces B31a, B31b, B31c, B31d, B31e & B31f of the strut B31 define the outer surface of the strut's elongate and somewhat cylindrical surface. Each of the elongate faces B31a, B31b, B31c, B31d, B31e & B31f are isosceles triangles with a first internal angle, angle A, and a second internal angle, angle B, where angle B is greater than angle A. The strut B31 also has two end faces B31f & B31g that isosceles triangles that are substantially similar to one another, having a first internal angle, angle C, and a second internal angle, angle D, and where angle D is greater than angle C. When comparing the internal angles of the elongate faces B31a, B31b, B31c, B31d, B31e & B31f to the end faces B31f & B31g, angle C is greater than angle A.

Figure 1J:
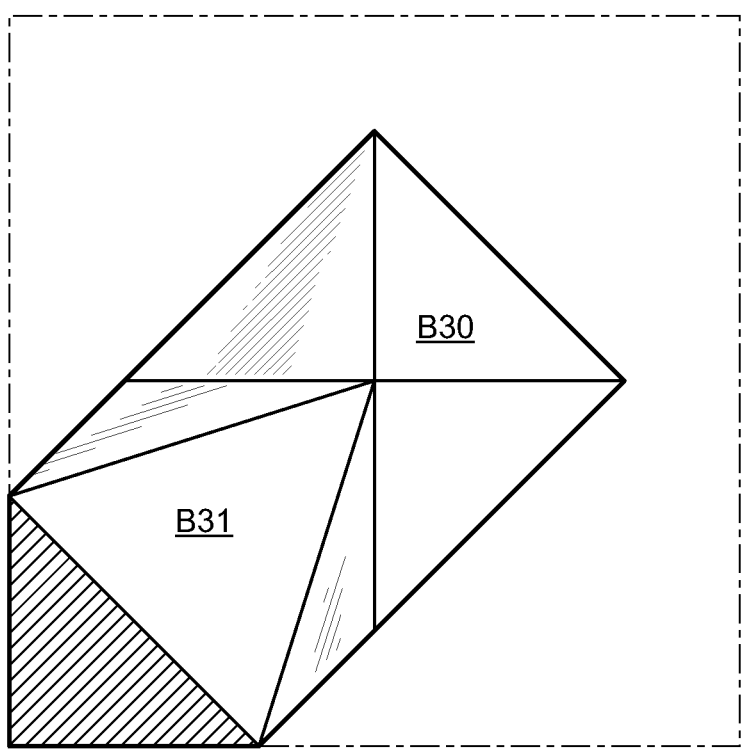
FIG. 1J is a side view of an example of a single node and single strut combination that could be used in a radial dodeca-rhombus unit cell.
Figure 1K:
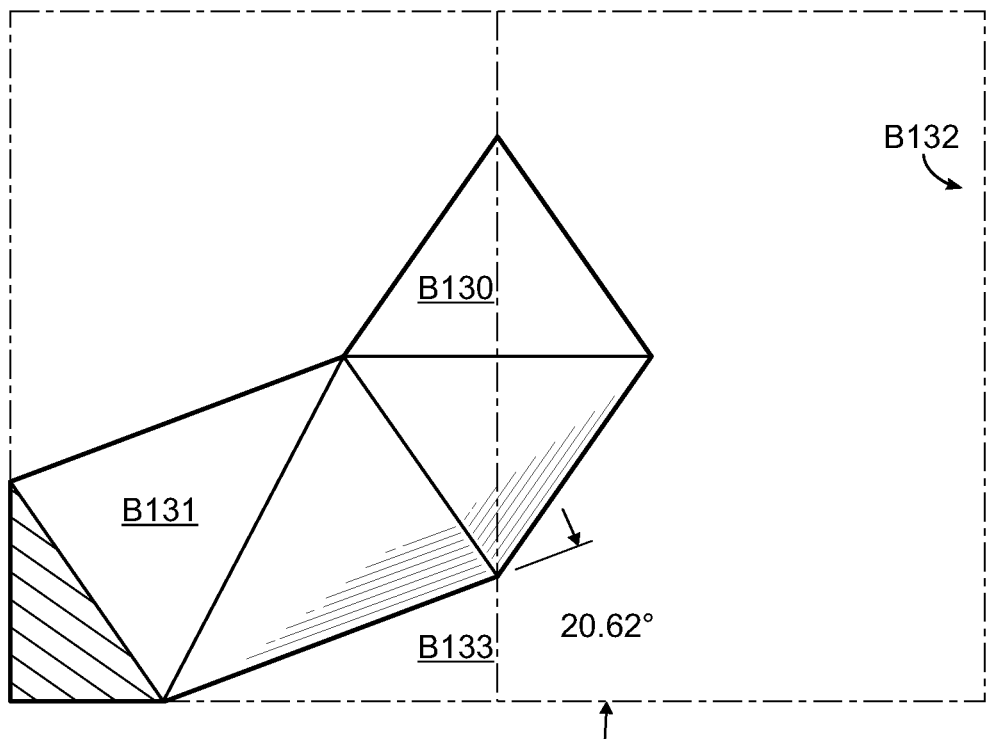
FIG. 1K is a side view of a single node and single strut combination configured for use in a lattice with an elastic modulus of approximately 3 GPa, viewed from the corner of the volume defining the bounds of the combination.
Figure 1L:
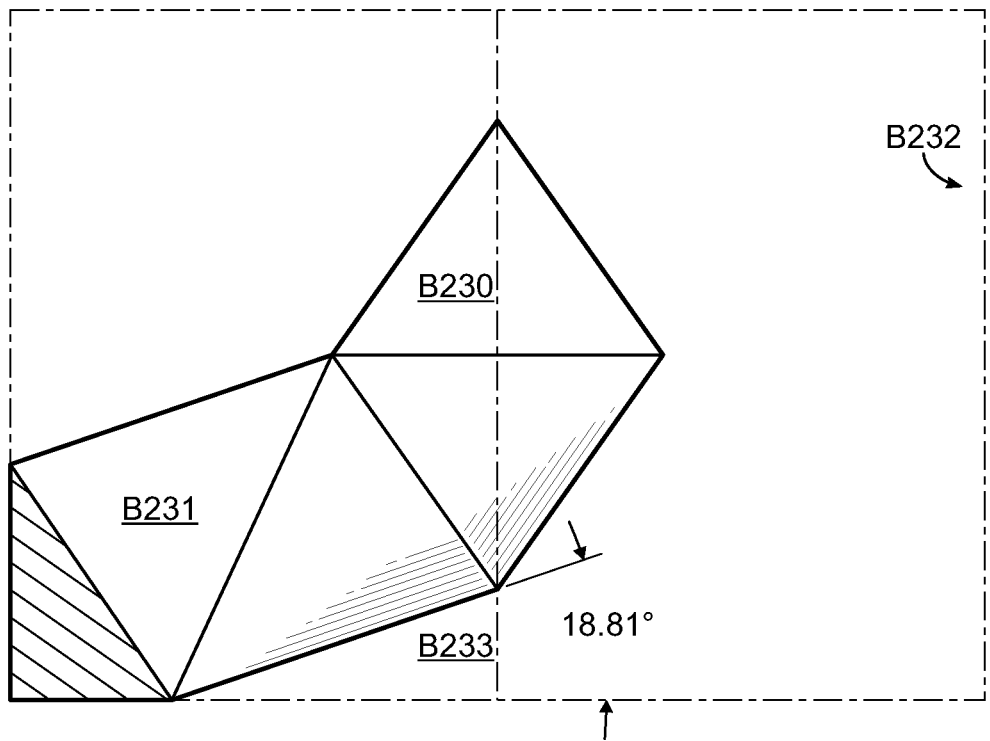
FIG. 1L is a side view of a single node and single strut combination configured for use in a lattice with an elastic modulus of approximately 4 GPa, viewed from the corner of the volume defining the bounds of the combination.
Figure 1M:
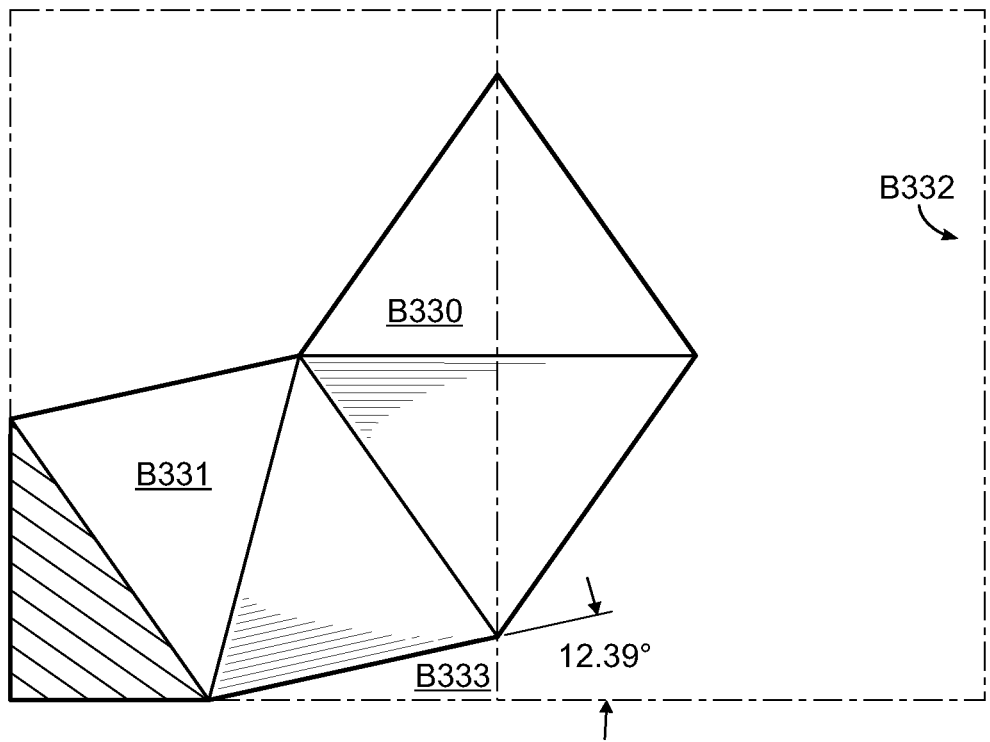
FIG. 1M is a side view of a single node and single strut combination configured for use in a lattice with an elastic modulus of approximately 10 GPa, viewed from the corner of the volume defining the bounds of the combination.

In FIG. 1J is a side view of the node B30 and strut B31 combination bounded by volume B32. In the side view, the height of the node B30 compared to the height of the cube B32 can be compared easily. In FIGS. 1K-1M are side views of node and strut combinations viewed from a corner of the volume rather than a wall or face, and where the combinations have been modified from FIGS. 1I-1J to change the volumetric density of the resulting unit cell. In FIG. 1K, the height of the node B130 has increased relative to the height of the volume B132. Since the distal end of the strut B131 is fixed by the location of a corner of the volume B132, the strut B131 must change its angle relative to its attached node face so that it becomes nonorthogonal. The node B130 and strut B131 combination, where the angle of the strut B131 from a horizontal plane is about 20.6 degrees, would be appropriate for a lattice structure with an elastic modulus of approximately 3 GPa.

In FIG. 1L, the height of the node B230 relative to the height of the cube B232 has been increased over the ratio of FIG. 1K to create a node B230 and strut B231 combination that would be appropriate for a lattice structure with an elastic modulus of approximately 4 GPa. As the height of the node B230 increases, the angle between the strut B231 and a horizontal plane decreases to about 18.8 degrees. As the height of the node B230 increases, the size of the node faces also increase so that the size of the strut B231 increases. While the distal end of the strut B231 is fixed to the corner of the volume B232, the size of the distal end increases to match the increased size of the node face to maintain a substantially even strut diameter along its length. As the node and strut increase in size, the volumetric density increases, as does the elastic modulus. In FIG. 1M, the height of the node B330 relative to the height of the volume B332 has been increased over the ratio of FIG. 1M to create a node B330 and strut B331 combination that would be appropriate for a lattice structure with an elastic modulus of approximately 10 GPa. In this configuration, the angle B333 between the strut B331 and a horizontal plane decreases to about 12.4 degrees and the volumetric density increases over the previous examples. The single node and strut examples can be copied and/or mirrored to create unit cells of appropriate sizes and characteristics. For instance, the angle between the strut and a horizontal plane could be increased to 25.8 degrees to render a lattice with a 12.3 percent volumetric density and an elastic modulus of about 300 MPa. While a single node and single strut were shown in the examples for clarity, multiple struts may be attached to each node to create an appropriate unit cell.

Adjacent struts extending from adjacent node faces on either the upper half or lower half of the node have an angle from the horizontal plane and a lateral separation angle defined by an angle between the strut directions of adjacent struts. In the MRDD and RDDR structures, adjacent struts have an external edge or face of the elongate portion extending closest to the relevant adjacent strut. The lateral separation angle, as used herein, generally refers to the angle between an external edge or face of the elongate portion of a strut extending closest to the relevant adjacent strut. In some embodiments, a lateral separation angle defined by a line extending between the center of the strut end faces or a line defined by the center of mass of the struts can be used in reference to a similar calculation for an adjacent strut.

Figure 1N:
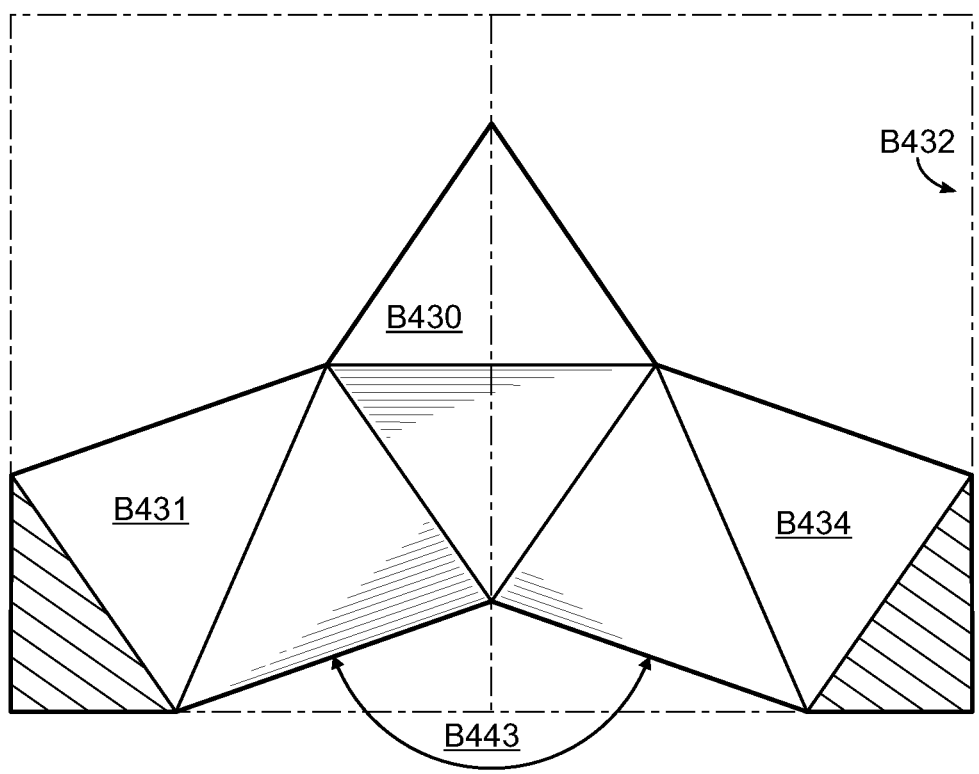
FIG. 1N is a side view of a single node and two adjacent struts viewed from the corner of the volume defining the bounds of the combination and the lateral separation angle.

The lateral separation angle is the angle between the nearest face or edge of a strut to an adjacent strut. The lateral separation angle can be measured as the smallest angle between the nearest edge of a strut to the nearest edge of an adjacent strut, in a plane containing both strut edges. The lateral separation angle can also be measured as the angle between the nearest face of a strut to the nearest face of an adjacent strut in a plane normal to the two strut faces. In embodiments without defined strut edges or strut faces, the lateral separation angle can be measured as an angle between the nearest portion of one strut to the nearest portion of an adjacent strut. For a unit cell in a cubic volume, as the strut angle from the horizontal plane decreases, the lateral separation angle approaches 90 degrees. For a unit cell in a cubic volume, as the strut angle from the horizontal plane increases, the lateral separation angle approaches 180 degrees. In some embodiments, it is preferable to have a lateral separation angle greater than 109.5 degrees. In some embodiments, it is preferable to have a lateral separation angle of less than 109.5 degrees. In some embodiments, it is preferable to have a lateral separation angle of between and including about 108 degrees to about 156 degrees. In some embodiments, it is more preferable to have a lateral separation angle of between and including 111 degrees to 156 degrees. In some embodiments, it is more preferable to have a lateral separation angle of between and including 108 degrees to 120 degrees. In some embodiments, it is most preferable to have a lateral separation angle of between and including about 111 degrees to 120 degrees. In some embodiments, it is more preferable to have a lateral separation angle of between and including 128 degrees to 156 degrees. In FIG. 1N is a side view, viewed from a corner of the cube B432, of a single node B430 with two adjacent struts B431 & B434 attached and where the lateral separation angle B443 is identified. When measured from the nearest edge of a strut to the nearest edge of an adjacent strut, the lateral separation angle B443 is about 116 degrees.

Figure 1Q:
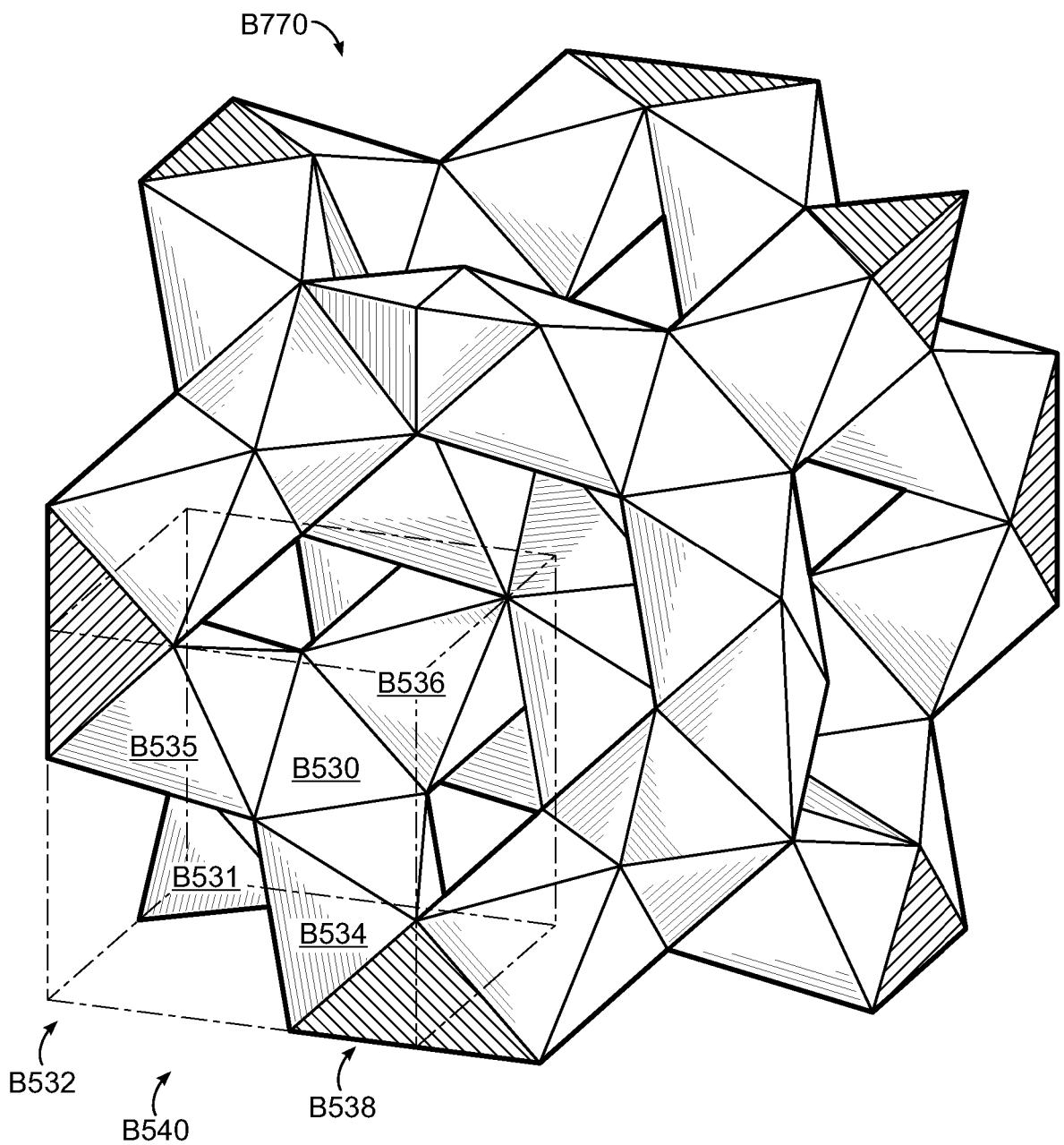
FIG. 1Q is an isometric view of eight sub-unit cells stacked together to form a single unit cell.

In some embodiments, a unit cell is built up from multiple sub-unit cells fixed together. In FIG. 1O is an isometric view of an exemplary sub-unit cell comprising a single node and four struts. In FIG. A16 is an isometric view of two sub-unit cells in a stacked formation where the upper sub-unit cell is inverted and fixed to the top of the lower sub-unit cell. In FIG. 1Q is an isometric view of eight sub-unit cells stacked together to form a single RDDR unit cell.

In FIG. 1O, the node B530 is a square bipyramid, oriented so that the two peaks face the top and bottom of a cubic volume B532. In some embodiments, the volume B532 can be a cuboid volume, a hexahedron volume, an amorphous volume or of a volume with one or more non-orthogonal sides. The peaks refer to the point where four upper faces meet and the point where four lower faces meet. The node B530 is oriented so that the horizontal vertices face the lateral sides of the cubic volume B532. The strut B531 is fixed to a lower face of the node B530 face on its proximate end and extends to the nearest corner of the cubic volume B532 at its distal end. The distal end of the strut B531 can remain fixed to the cubic volume B532 even if the node B530 changes in size to adjust the sub-unit cell properties.

On the lower face of the node B530 opposite the face which strut B531 is fixed, the proximate end of strut B534 is fixed to the node B530. The strut B534 extends to the nearest corner of cubic volume B532 at its distal end. The strut B535 is fixed on its proximate end to an upper node B530 face directed about 90 degrees laterally from the node B530 face fixed to strut B531. The strut B535 extends to the nearest corner of the cubic volume B532 at its distal end. On the upper face of the node B530 opposite the face which strut B535 is fixed, the proximate end of strut B536 is fixed to the node B530. The strut B536 extends to the nearest corner of the cubic volume B532 at its distal end.

In some embodiments, the struts B531 & B534-B536 are octahedrons with triangular faces. The strut face fixed to a node B530 face can be substantially the same size and orientation of the node B530 face. The strut face fixed to the nearest corner of the cube B532 can be substantially the same size as the strut face fixed to the node B530 and oriented on a substantially parallel plane. The remaining six faces can be six substantially similar isosceles triangles with a first internal angle and a second internal angle larger than said first internal angle. The six substantially similar isosceles triangles can be fixed along their long edges to an adjacent and inverted substantially similar isosceles triangle to form a generally cylindrical shape with triangular ends.

When forming a sub-unit cell B540, it can be beneficial to add an eighth node B538 to each corner of the cube B532 fixed to a strut B531 & B534-B536. When replicating the sub-unit cell B540, the eighth node B538 attached to each strut end is combined with eighth nodes from adjacent sub-unit cells to form nodes located between the struts of adjacent sub-unit cells.

In FIG. A16 is a first sub-unit cell B540 fixed to a second sub-unit cell B640 to form a quarter unit cell B560 used in some embodiments. The second sub-unit cell B640 comprises a square bipyramid node B630 is a square bipyramid, oriented so that the two peaks face the top and bottom of a cubic volume. The node B630 is oriented so that the horizontal vertices face the lateral sides of the cubic volume. The strut B635 is fixed to a lower face of the node B630 face on its proximate end and extends to the nearest corner of the cubic volume at its distal end. On the lower face of the node B630 opposite the face which strut B635 is fixed, the proximate end of strut B636 is fixed to the node B630. The strut B636 extends to the nearest corner of cubic volume at its distal end. The strut B634 is fixed on its proximate end to an upper node B630 face directed about 90 degrees laterally from the node B630 face fixed to strut B635. The strut B634 extends to the nearest corner of the cubic volume at its distal end. On the upper face of the node B630 opposite the face which strut B634 is fixed, the proximate end of strut B631 is fixed to the node B630. The strut B631 extends to the nearest corner of the cubic volume at its distal end.

The first sub-unit B540 is used as the datum point in the embodiment of FIG. A16, however, it is appreciated that the second sub-unit cell B640 or another point could also be used as the datum point. Once the first sub-unit cell B540 is fixed in position, it is replicated so that the second sub-unit cell B640 is substantially similar to the first. The second sub-unit cell B640 is rotated about its central axis prior to being fixed on the top of the first unit-cell B540. In FIG. A16, the second sub-unit cell B640 is inverted to achieve the proper rotation, however, other rotations about the central axis can achieve the same result. The first sub-unit cell B540 fixed to the second sub-unit cell B640 forms a quarter unit cell B560 that can be replicated and attached laterally to other quarter unit cells to form a full unit cell.

Alternatively, a full unit cell can be built up by fixing a first group of four substantially similar sub-unit cells together laterally to form a square, rectangle or quadrilateral when viewed from above. A second group of four substantially similar sub-unit cells rotated about their central axis can be fixed together laterally to also form a square, rectangle or quadrilateral when viewed from above. The second group of sub-unit cells can be rotated about their central axis prior to being fixed together laterally or inverted after being fixed together to achieve the same result. The second group is then fixed to the top of the first group to form a full unit cell.

In FIG. 1Q is an example of a full unit cell B770 formed by replicating the sub-unit cell B540 of FIG. 1O. The cube B532 defining the bounds of the sub-unit cell B540 is identified as well as the node B530 and struts B531 & B534-B536 for clarity. The full unit cell B770 of FIG. 1Q can be formed using the methods described above or using variations within the inventive concept.

Each strut extending from the node, for a given unit cell, can be substantially the same length and angle from the horizontal plane, extending radially from the node. At the end of each strut, the strut is mirrored so that struts extending from adjacent node faces form a rhombus shaped opening. Because the struts can be non-orthogonal to the node faces, rhombuses of two shapes emerge. In this configuration, a first group of four rhombuses extend radially from the node oriented in vertical planes. The acute angles of the first group of rhombuses equal twice the strut angle from the horizontal plane and the obtuse angles equal 180 less the acute angles. Also in this configuration is a second group of eight rhombuses extending radially so that a portion of the second group of eight rhombuses fall within the lateral separation angle between adjacent struts defining the first group of four rhombuses. The acute angles of the second group of rhombuses can be about the same as the lateral separation angle between adjacent struts that define the first group of four rhombuses and the obtuse angles equal 180 less the acute angles. The characteristics of a scaffold may also be described by its surface area per volume. For a 1.0 mm×1.0 mm×1.0 mm solid cube, its surface area is 6.0 square mm. When a 1.0 cubic mm structure is comprised of a lattice structure rather than a 100 percent volumetric density material, the surface area per volume can increase significantly. In low volumetric density scaffolds, the surface area per volume increases as the volumetric density increases. In some embodiments, a scaffold with a volumetric density of 30.1 percent would have a surface area of 27.4 square mm per cubic mm. In some embodiments, if the volumetric density was decreased to 27.0 percent, the lattice would have a surface area of 26.0 square mm per cubic mm and if the volumetric density were decreased to 24.0 percent, the lattice would have a surface area of 24.6 square mm per cubic mm.

The MRDD and RDDR structures disclosed herein also have the advantage of an especially high modulus of elasticity for a given volumetric density. When used as a lattice or scaffold, an implant with an adequate modulus of elasticity and a low volumetric density can be achieved. A low volumetric density increases the volume of the implant available for bone ingrowth.

In Table 1, below, are a number of example lattice configurations of various lattice design elastic moduli. An approximate actual elastic modulus was given for each example, representing a calculated elastic modulus for that lattice after going through the manufacturing process. The lattice structures and implants disclosed herein can be designed to a design elastic modulus in some embodiments and to an approximate actual elastic modulus in other embodiments. One advantage of the presently disclosed lattice structures is that the approximate actual elastic modulus is much closer to the design elastic modulus than has been previously achieved. During testing, one embodiment of a lattice was designed for a 4.0 GPa design elastic modulus. Under testing, the lattice had an actual elastic modulus of 3.1 GPa, achieving an actual elastic modulus within 77 percent of the design elastic modulus.

For each lattice design elastic modulus, a volumetric density, ratio of design elastic modulus to volumetric density, surface area in $mm^2$, ratio of surface area to volumetric density and ratio of surface area to lattice design elastic modulus is given.

In some of the embodiments disclosed herein, the required strut thickness can be calculated from the desired modulus of elasticity. Using the following equation, the strut thickness required to achieve a particular elastic modulus can be calculated for some MRDD and RDDR structures:

Strut Thickness=$(-0.0035*(E^2))+(0.0696*E)+0.4603$

In the above equation, "E" is the modulus of elasticity. The modulus of elasticity can be selected to determine the required strut thickness required to achieve that value or it can be calculated using a preselected strut thickness. The strut thickness is expressed in mm and represents the diameter of the strut. The strut thickness may be calculated using a preselected modulus of elasticity or selected to determine the modulus of elasticity for a preselected strut thickness.

In some embodiments, the unit cell can be elongated in one or more directions to provide a lattice with anisotropic properties. When a unit cell is elongated, it generally reduces the elastic modulus in a direction normal to the direction of the elongation. The elastic modulus in the direction of the elongation is increased. It is desirable to elongate cells in the direction normal to the direction of new bone growth contained within the interconnections, openings and central voids (if any). By elongating the cells in a direction normal to the desired direction of reduced elastic modulus, the shear strength in the direction of the elongation may be increased, providing a desirable set of qualities when designing a structural scaffold. Covarying the overall stiffness of the scaffold may augment or diminish this effect, allowing variation in one or more directions.

In some embodiments, the sub-unit cells may be designing by controlling the height of the node relative to the height of the volume that defines the sub-unit cell. Controlling the height of the node can impact the final characteristics and appearance of the lattice structure. In general, increasing the height of the node increases the strut thickness, increases the volumetric density, increases the strength and increases the elastic modulus of the resulting lattice. When increasing the height of the node, the width of the node can be held constant in some embodiments or varied in other embodiments.

In some embodiments, the sub-unit cells may be designing by controlling the volume of the node relative to the volume that defines the sub-unit cell. Controlling the volume of the node can impact the final characteristics and appearance of the lattice structure. In general, increasing the volume of the node increases the strut thickness, increases the volumetric density, increases the strength and increases the elastic modulus of the resulting lattice. When increasing

TABLE 1

Table of example lattice structures based on lattice design elastic modulus in GPa

| Lattice Design Elastic Modulus (GPa) | Approx. Actual Elastic Modulus (GPa) | Volumetric Density (percent) | Ratio of Design Elastic Modulus to Volumetric Density | Surface Area ($mm^2$) | Ratio of Surface Area to Volumetric Density | Ratio of Surface Area to Lattice Design Elastic Modulus |
|---|---|---|---|---|---|---|
| 0.3 | 0.233 | 18.5 | 1.6 | 22.5 | 121.5 | 74.9 |
| 3 | 2.33 | 29.9 | 10.0 | 27.5 | 92.2 | 9.2 |
| 4 | 3.10 | 33.4 | 12.0 | 28.8 | 86.4 | 7.2 |
| 5 | 3.88 | 36.4 | 13.8 | 29.9 | 82.2 | 6.0 |
| 6 | 4.65 | 38.8 | 15.5 | 30.7 | 79.1 | 5.1 |
| 7 | 5.43 | 40.8 | 17.2 | 31.3 | 76.9 | 4.5 |
| 8 | 6.20 | 42.1 | 19.0 | 31.8 | 75.4 | 4.0 |
| 9 | 6.98 | 43.2 | 20.8 | 32.1 | 74.3 | 4.0 | the volume of the node, the width or height of the node could be held constant in some embodiments.

In Table 2, below, are a number of example lattice configurations of various lattice design elastic moduli. An approximate actual elastic modulus was given for each example, representing a calculated elastic modulus for that lattice after going through the manufacturing process. The lattice structures and implants disclosed herein can be designed to a design elastic modulus in some embodiments and to an approximate actual elastic modulus in some embodiments. For each lattice design elastic modulus, a lattice approximate elastic modulus, a node height, a volumetric density, a node volume, a ratio of node height to volumetric density, a ratio of node height to lattice design elastic modulus and a ratio of volumetric density to node volume is given.

The disclosed structures can also have benefits when used in applications where osteointegration is not sought or undesirable. By including a growth inhibiting coating or skin on a structure, the lattice disclosed herein can be used to provide structural support without providing a scaffold for bone growth. This may be desirable when used in temporary implants or medical devices that are intended to be removed after a period of time.

Disclosed herein is a first exemplary embodiment of a fixation plate 10 configured for use with an exemplary implant 20. The fixation plate can be configured to work with multiple types of implants, including but not limited to, bone fusion implants and interbody fusion implants. In some embodiments, the implant 20 is a cervical stand-alone (hereinafter "CSA") implant. In some embodiments, the implant 20 is an Anterior Lumbar Interbody Fusion Stand-Alone

TABLE 2

Table of example lattice structures based on lattice design elastic modulus in GPa

| Lattice Design Elastic Modulus (GPa) | Lattice Approx. Actual Elastic Modulus (GPa) | Node Height (mm) | Volumetric Density (percent) | Node Volume (mm3) | Ratio of Node Height to Vol. Density | Ratio of Node Height to Lattice Design Elastic Modulus | Ratio of Vol. Density to Node Volume |
|---|---|---|---|---|---|---|---|
| 0.30 | 0.23 | 0.481 | 18.5 | 0.0185 | 2.60 | 1.60 | 9.98 |
| 3.00 | 2.33 | 0.638 | 29.9 | 0.0432 | 2.14 | 0.21 | 6.91 |
| 4.00 | 3.10 | 0.683 | 33.4 | 0.0530 | 2.05 | 0.17 | 6.29 |
| 5.00 | 3.88 | 0.721 | 36.4 | 0.0624 | 1.98 | 0.14 | 5.82 |
| 6.00 | 4.65 | 0.752 | 38.8 | 0.0709 | 1.94 | 0.13 | 5.48 |
| 7.00 | 5.43 | 0.776 | 40.8 | 0.0779 | 1.90 | 0.11 | 5.23 |
| 8.00 | 6.20 | 0.793 | 42.1 | 0.0831 | 1.88 | 0.10 | 5.07 |
| 9.00 | 6.98 | 0.807 | 43.2 | 0.0877 | 1.87 | 0.09 | 4.93 |

Some embodiments of the disclosed lattice structures are particularly useful when provided within an elastic modulus range between an including 0.375 GPa to 4 GPa. Some embodiments, more preferably, include a lattice structure with an elastic modulus between and including 2.5 GPa to 4 GPa. Some embodiments include a lattice structure with a volumetric density between and including five percent to 40 percent. Some embodiments, more preferably, include a lattice structure with a volumetric density between and including 30 percent to 38 percent.

The lattice structures disclosed herein have particularly robust loading and fatigue characteristics for low volumetric density ranges and low elastic moduli ranges. Some embodiments of the lattice structures have a shear yield load and a compressive yield load between and including 300 to 15000N in static and dynamic loading up to 5,000,000 cycles at 5 Hz. Some embodiments have a compressive shear strength and an axial load between and including 300 to 15000N in static and dynamic loading up to 5,000,000 cycles at 5 Hz. Some embodiments have a shear strength and an axial load between and including 300 to 15000N in static and dynamic loading up to 5,000,000 cycles at 5 Hz. Some embodiments have a torsional yield load up to 15 Nm.

In one example, the inventive lattice structure has a volumetric density of between and including 32 percent to 38 percent, an elastic modulus between and including 2.5 GPa to 4 GPa and a shear strength and an axial load between and including 300 to 15000N in static and dynamic loading up to 5,000,000 cycles at 5 Hz. Some examples include a first set of substantially homogeneous openings with a width of about 200 μm to 900 μm and a second set of substantially homogenous openings with a width of about 1 to 15 times the width of the first set of openings, where the number of openings in the second set are provided at a ratio of about 1:8 to 1:12 relative to the number of openings in the first set.

(hereinafter "ALIF-SA") implant. In some embodiments, the implant 20 is a Posterior Lumbar Interbody Fusion (hereinafter "PLIF") implant. In some embodiments, the implant 20 is a Transforaminal Lumbar Interbody Fusion (hereinafter "TLIF") implant. In some embodiments, the implant 20 is a PLIF or TLIF implant. In some embodiments, the implant 20 is an Anterior Lumbar Interbody Fusion (hereinafter "ALIF") implant. In some embodiments, the implant 20 is a vertebral body replacement (hereinafter "VBR") implant. In some embodiments, the implant 20 is an osteotomy wedge. In some embodiments, the implant 20 is an ankle fusion spacer implant. In some embodiments, the implant 20 is configured for tissue attachment, tissue including but not limited to bony structures and connective tissue. In some embodiments, the implant 20 is configured to allow tissue in-growth, tissue including but not limited to bony structures and connective tissue.

The fixation plate 10 can be configured to allow motion relative to an implant after implantation and/or relative to a patient's tissue after implantation. In some embodiments, the fixation plate can allow axial compression relative to an implant after implantation. In the embodiment of the fixation plate presented, the fixation plate can be attached to the implant so that the fixation plate has at least one degree of freedom relative to the implant. The fixation plate can also be attached to a first bone and/or a second bone, each attachment with at least one degree of freedom. In some embodiments, the fixation plate can be attached to an implant and/or tissue so that the fixation plate has more than one degree of freedom relative to its respective attachment point. In some embodiments, the fixation plate can be attached to a first bone and/or a second bone with a conical degree of freedom.

Some embodiments of the fixation plate have screw holes with a concave profile and are attached to a patient's bone using a bone screw with a screw head having a convex profile, corresponding to the concave profile of the screw holes, when viewed from the side on the end of the screw head oriented towards the threaded portion. The use of a screw head with a convex profile and a screw hole with a concave profile can provide a fixation with at least a conical degree of freedom. The bone screw head can also be fixed relative to the fixation plate screw holes with a clearance fit of greater than zero that can provide, in some respects, an amount of translational motion and prevent binding between the bone screw head and fixation plate screw holes. A clearance fit, as used herein, refers to a condition where there is a positive difference between the dimensions of assembled components. For example, a clearance fit would be present when the diameter of a screw head is less than its corresponding screw hole.

The fixation plate can be attached to an implant using a fastening means with at least one degree of freedom. Some embodiments of the fixation plate use a fastening means with a clearance fit of greater than zero between the fixation plate and an implant. The use of a fastening means with a clearance fit can provide, in some respects, an amount of translational motion and prevent binding between the fixation plate, the implant and/or the fastening means. Some fastening means that could be used include, but are not limited to, quarter turn fasteners, screws, etc. A clearance fit with respect to a quarter turn fastener can be in an axial and/or radial direction, providing multiple directions for translational motion.

The number of degrees of freedom provided between two given components can be the result of multiple factors, including but not limited to, a designed degree of freedom, a manufacturing tolerance degree of freedom or a clearance fit degree of freedom. The disclosure focuses on a designed degree of freedom and, in some embodiments, an intended clearance fit degree of freedom. However, it is appreciated that manufacturing tolerances can be measured and/or measured and used similarly to create a device with the necessary degree(s) of freedom.

Figure 1R:
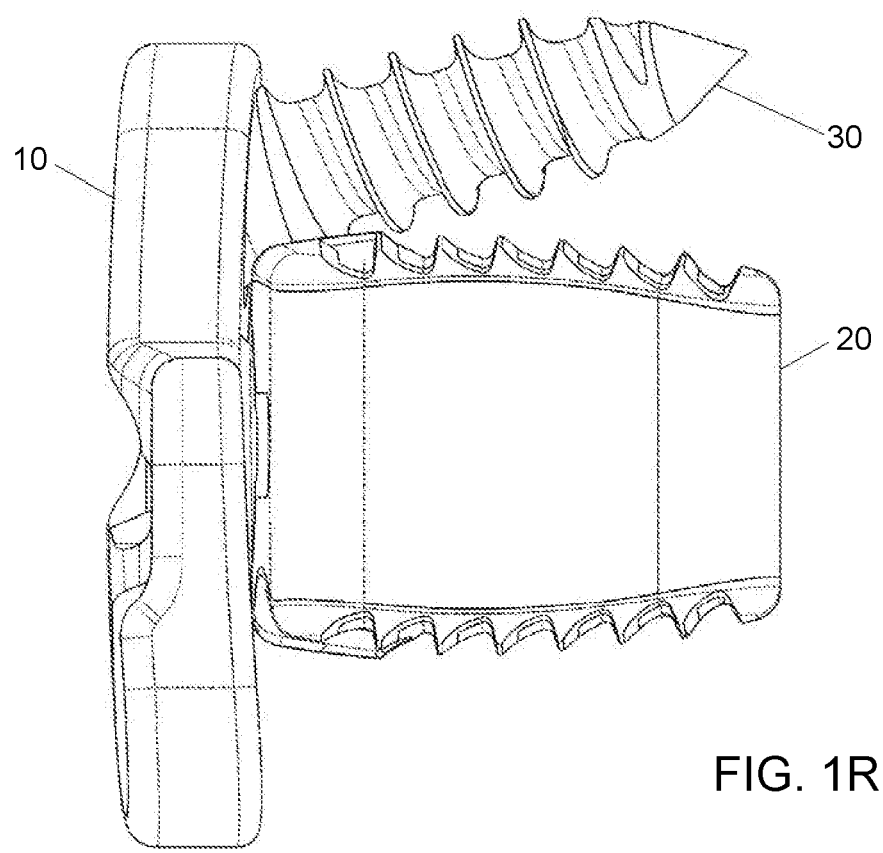
FIG. 1R is a side view of a bone fixation plate, a bone screw and an implant.

In FIG. 1R is a side view of the fixation plate 10 rotatably attached to an implant 20. One bone screw 30 is pictured, however the fixation plate 10 is configured for two bone screws to be used. In FIG. 1R, the fixation plate 10 is in a locked position relative to the implant 20. A locked position, as used herein, refers to one element being fixed to another element in at least one plane, but with freedom to move in at least one plane. In FIG. 1R, the fixation plate 10 is fixed in the forward to rear direction relative to the implant 20 but is free to rotation about an axis in the forward to rear direction. Forward and rear, are exemplary directions used to describe the drawings and are not intended to create any limitations as to use or configuration. In the drawings used herein, the rear of the implant 20 refers to the end of the implant 20 configured to accept the fixation plate 10. The front of the implant 20 refers to the end opposite the rear. Portions of the implant between the front and rear of the implant 20 can be described as lateral. The top to bottom direction of the implant 20 is described as the axial direction or the direction of compression. While the exemplary fixation plate 10 and implant 20 are configured for a situation where the axial direction and direction of compression are about the same, they do not need to be the same or similar.

Figure 2:
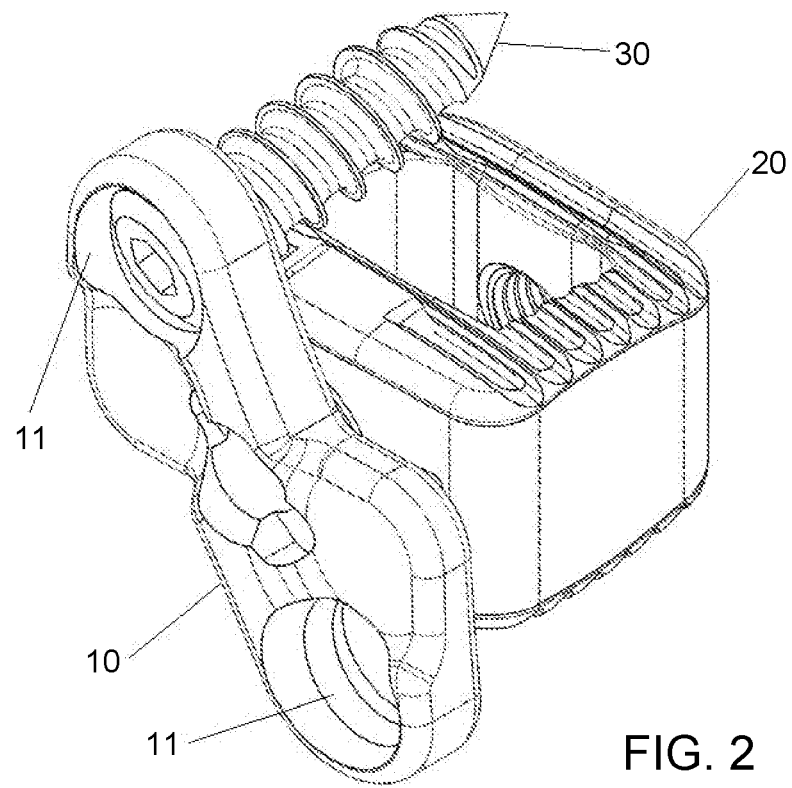
FIG. 2 is an isometric view of a bone fixation plate, a bone screw and an implant.

In FIG. 2 is an isometric view of the fixation plate 10, implant 20 and bone screw 30 in a locked position. The fixation plate 10 can be configured to rotate relative to the implant 20 about an axis located in the forward to rear direction. The angle of permitted rotation between the fixation plate 10 and the implant 20 can be limited by the interference between the implant 20 and a bone screw 30. The amount of axial compression permitted by the fixation plate 10 can be adjusted based on the placement of the bone screws 30 relative to the implant 20. As the bone screws 30 are spaced away from the implant 20 axially, the amount of axial compression permitted increases to a certain point. The amount of axial compression allowed can be approximated by the angle of the fixation plate 10 relative to the implant 20 after implantation for a fixation plate 10 of a particular length between screw holes 11. For example, a fixation plate 10 with 10 mm spacing between the screw hole centers 11 would allow more axial compression if implanted at an angle of 50 degrees relative to the implant 20 than if implanted at an angle of 45 degrees relative to the implant 20.

In some embodiments, the fixation plate 10 is oriented relative to the implant 20 based on a line drawn between the centers of the screw holes 11 relative to a plane passing through the axial center of the implant 20. In some embodiments, the fixation plate 10 is oriented between and including −45 degrees and 45 degrees relative to the implant 20 in an unlocked position. In some embodiments, the fixation plate 10 is oriented between and including 10 degrees and 90 degrees relative to the implant 20 in a locked position. In some embodiments, the fixation plate is oriented between and including −10 degrees and −90 degrees relative to the implant 20 in a locked position.

Figure 3:
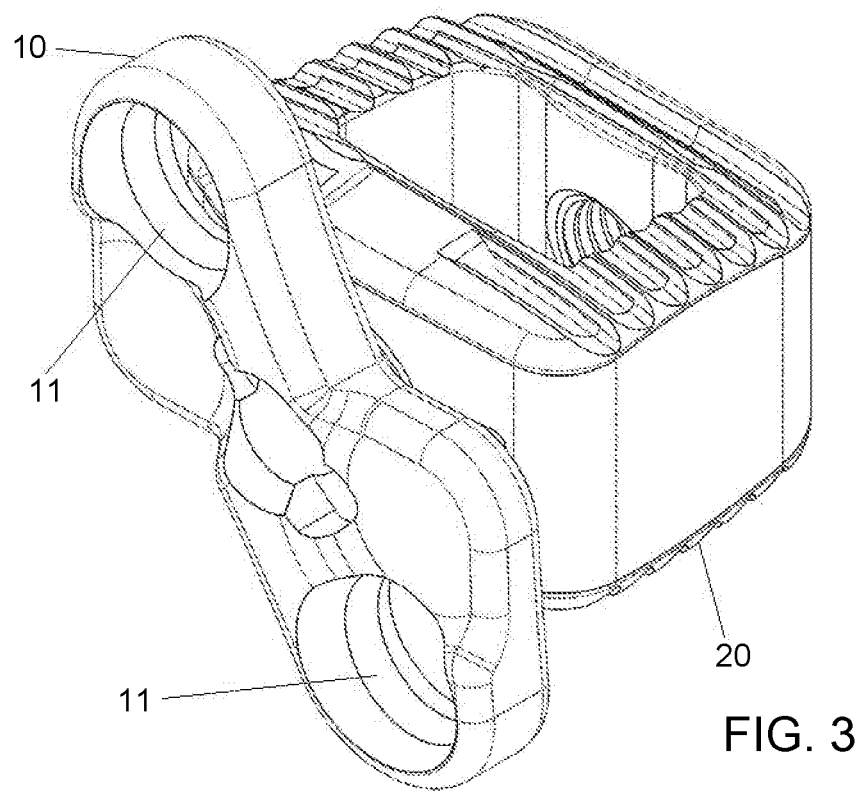
FIG. 3 is an isometric view of a bone fixation plate and an implant.
Figure 4:
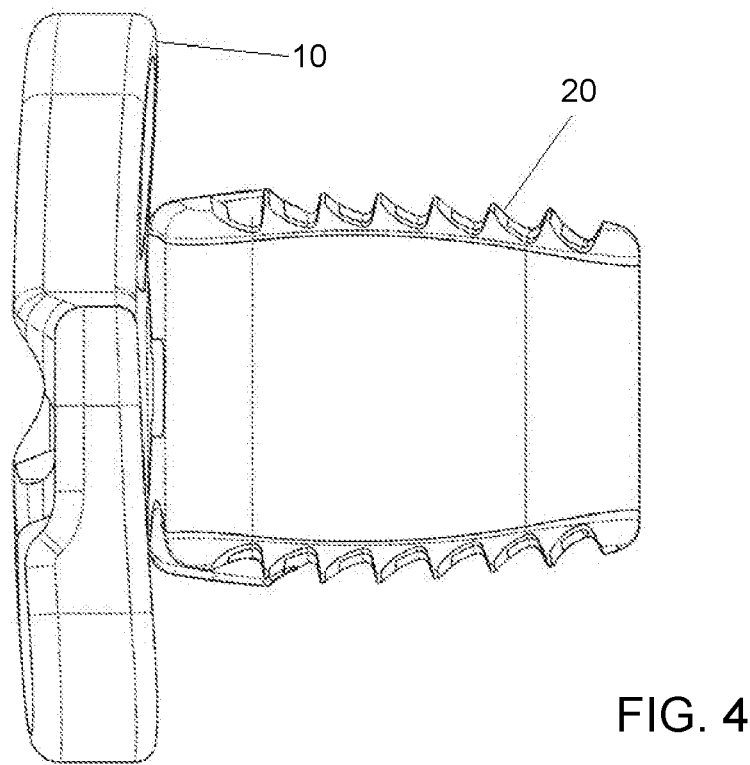
FIG. 4 is a side view of a bone fixation plate and an implant.

In FIGS. 3 and 4 are additional views showing the relationship between the fixation plate 10 and implant 20 in a locked position. While only one locked position is shown in the figures, it is appreciated that the fixation plate 10 could be rotated more or less relative to the implant 20 in this and other embodiments.

Figure 4A:
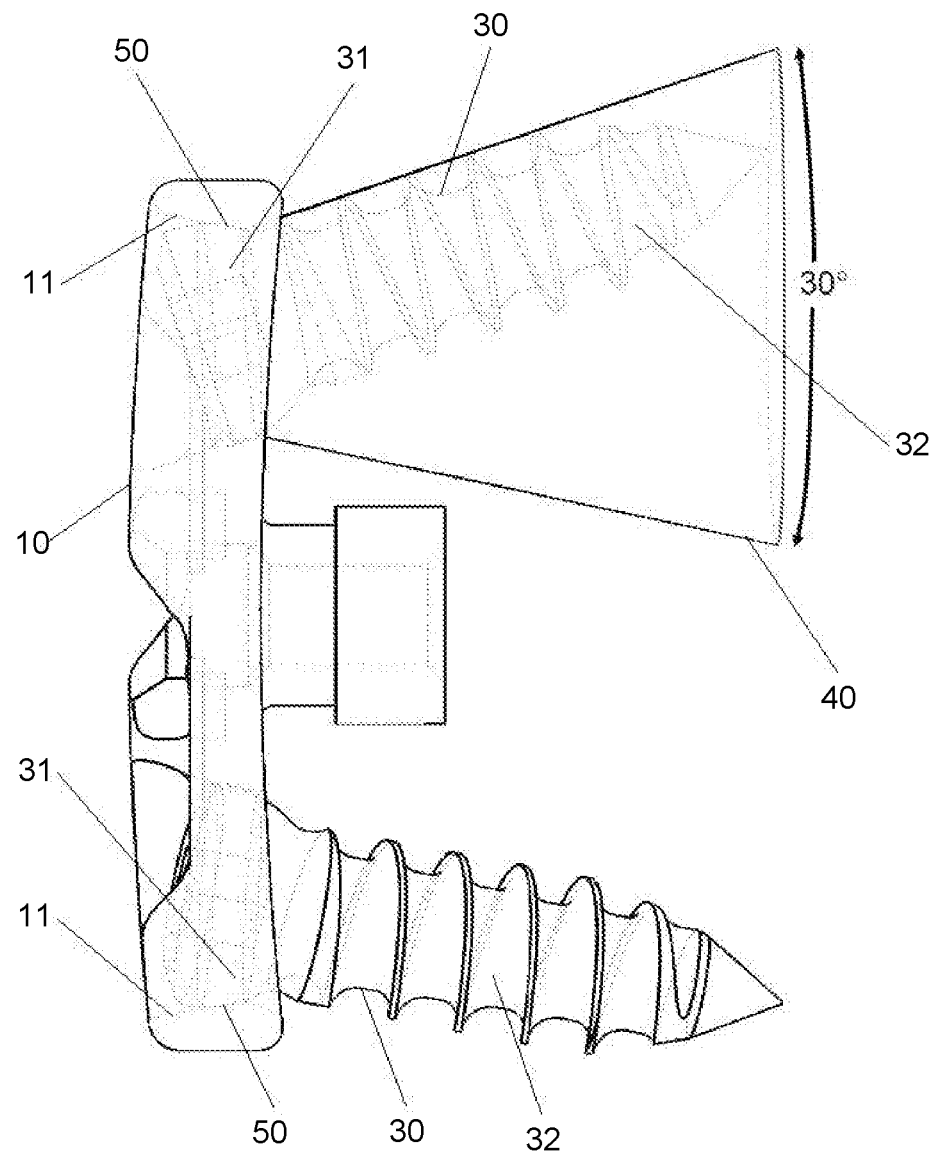
FIG. 4A is a side view of the bone fixation plate and two bone screws with hidden features shown in broken lines.

In FIG. 4A is a side view of the fixation plate 10 and bone screws 30 where hidden features are shown in broken lines. In some embodiments, the bone screws 30 can have a screw head 31 with a varying diameter that corresponds to a varying diameter of the screw holes 11. In some embodiments, the screw head 31 can have a convex profile when viewed from the side on the end of the screw head oriented towards the threaded portion 32. In some embodiments, the screw holes 11 can have a concave profile that corresponds to the convex profile of the screw head 31.

The use of a screw head 31 with a convex profile and a screw hole 11 with a concave profile can provide a fixation with at least a conical degree of freedom 40. While the use of a screw head 31 with a convex profile and a screw hole 11 with a concave profile is disclosed herein to provide a fixation with a conical degree of freedom, it is appreciated that other methods exist in the art to achieve a fixation with similar properties. In some embodiments, the conical degree of freedom is between zero degrees and 90 degrees. In some embodiments, the conical degree of freedom is between and including 10 degrees and 70 degrees. In some embodiments, the conical degree of freedom is between and including 20 and 40 degrees. In some embodiments, the conical degree of freedom is between and including 25 and 35 degrees. In some embodiments, the conical degree of freedom is between and including 28 degrees and 32 degrees. In some embodiments, the conical degree of freedom is about 30 degrees.

The use of a screw head 31 with a convex profile and a screw hole 11 with a concave profile can also provide a fixation with an infinite number of degrees of freedom. In some embodiments, the bone screw 30 is fixed to a segment of tissue so that there is a clearance fit 50 between the screw head 31 and the screw hole 11. The clearance fit 50 allows the fixation plate 10 to rotate relative to the screw head 31 along any designed degree of freedom and an amount in the direction of the clearance fit 50. In some embodiments, it is desirable to use a clearance fit 50 of greater than zero between the screw head 31 and the screw hole 11 to prevent binding.

In some embodiments, the screw holes 11 are circular and smooth internally to allow the fixation plate 10 to rotate relative to the bone screws 30. The screw holes 11 can have a single diameter or a diameter gradient to accept specifically shaped bone screws 30. The screw holes 11 and bone screws 30 can optionally be configured to include rotational stops to constrain the rotation of the fixation plate 10 relative to a bone screw 30.

Figure 5:
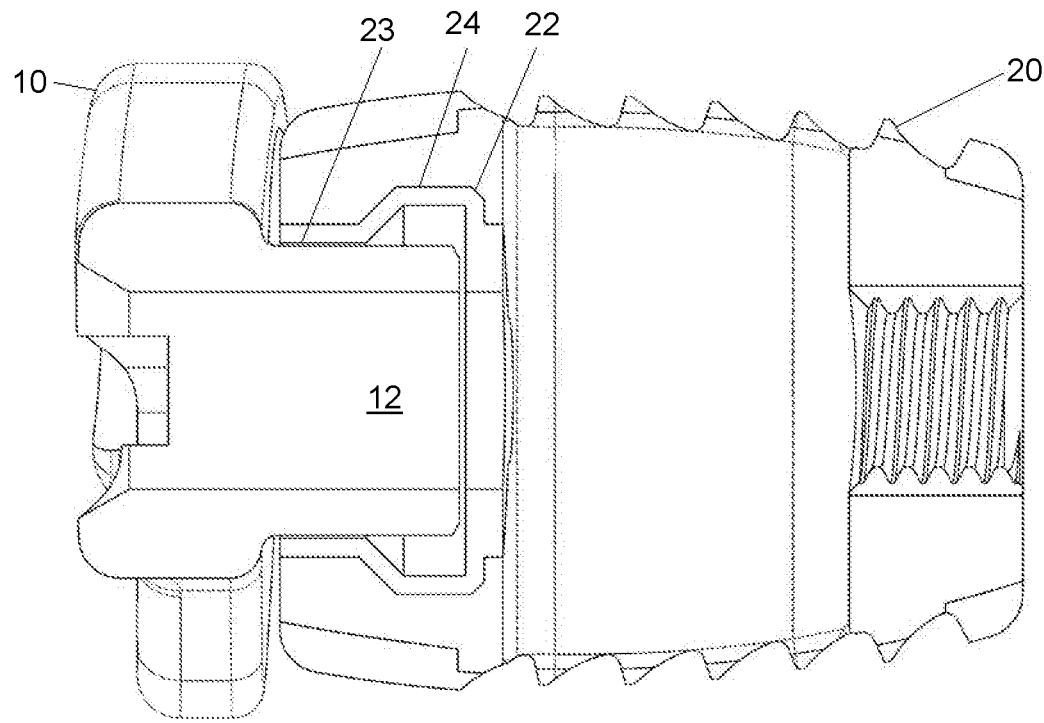
FIG. 5 is a side sectioned view of a bone fixation plate and an implant.

In FIG. 5 is a side sectioned view of the fixation plate 10 and implant 20 in an unlocked position. The fixation plate 10 further comprises a cylindrical member 12 configured to fit within an attachment port 22 in the implant 20. In some embodiments, the cylindrical member 12 and attachment port 22 further comprise a quarter locking mechanism using the partial rotation of the cylindrical member 12 or attachment port 22 relative to one another to engage a pin, wedge or tip on either with a surface configured to receive a pin, wedge or tip.

In the exemplary embodiment, the attachment port 22 further comprises an outer portion 23 and an inner portion 24. In some embodiments, the outer portion 23 is cylindrical, having a smaller diameter than the inner portion 24, also being cylindrical. The outer portion 24 can have one or more circular sectors where material has been removed in a radial direction that corresponds to areas on the cylindrical member 12 where material has been added in a radial direction. Material being added or removed can refer to the design process of a device or a process during manufacturing so that a device with material added can refer to a single continuous material and a device with material removed can refer to a device as manufactured.

Figure 6:
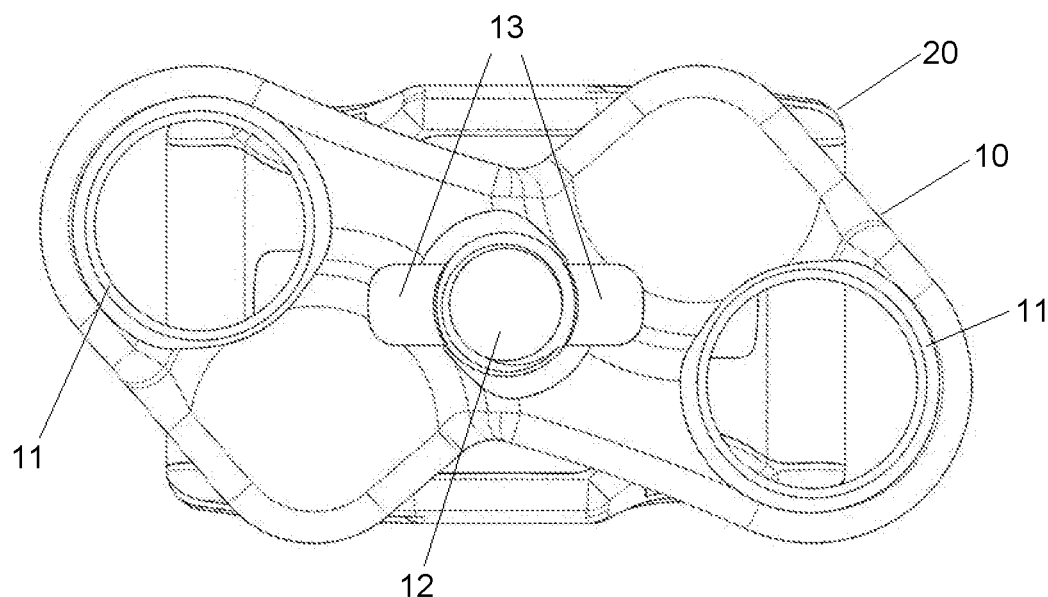
FIG. 6 is a rear view of a bone fixation plate and an implant.

In FIG. 6 is a rear view of the fixation plate 10 and implant 20 in an unlocked position. In some embodiments, tool engagement areas 13 can be included on the fixation plate 10 to apply a torque to the fixation plate 10 during implantation. A tool with extensions corresponding to the tool engagement areas 13 could be used to rotate the fixation plate 10.

Figure 7:
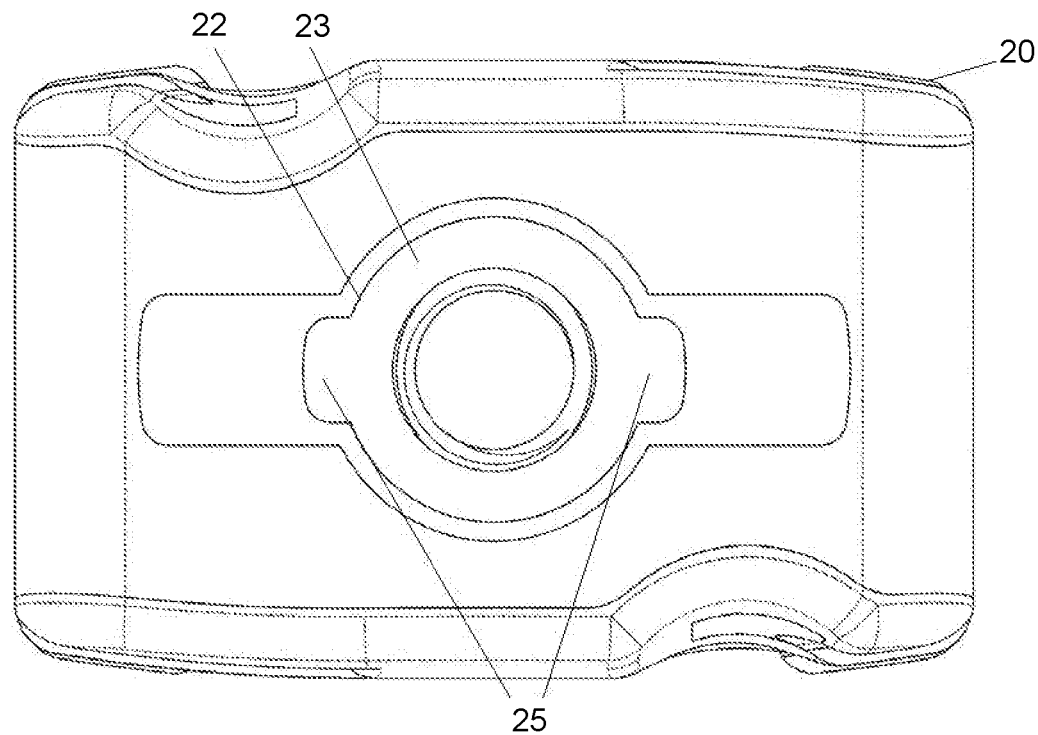
FIG. 7 is a rear view of an implant configured to receive the bone fixation plate.

In FIG. 7 is a rear view of the implant 20 configured to receive the fixation plate 10. In the exemplary embodiment, the cylindrical member 12 further comprises two pins 14 extending radially in opposite directions. The implant 20, in this embodiment, is configured to accept the two pins 14 through the inclusion of cutouts 25 extending radially in opposite directions in the outer portion 23 of the attachment port 22. It is appreciated that the disclosed configuration of pins and cutouts is merely one way to attach a fixation plate 10 to an implant 20 in a way to allow an unlocked and a locked position. For example, fewer or greater than two pins 14 could be used, fewer or greater than two cutouts 25 could be used, the pins 14 could be spaced apart on the cylindrical member 12 at an interval other than about 180 degrees and the cutouts 25 could be spaced apart on the outer portion of the attachment port 22 at an interval other than about 180 degrees.

Figure 8:
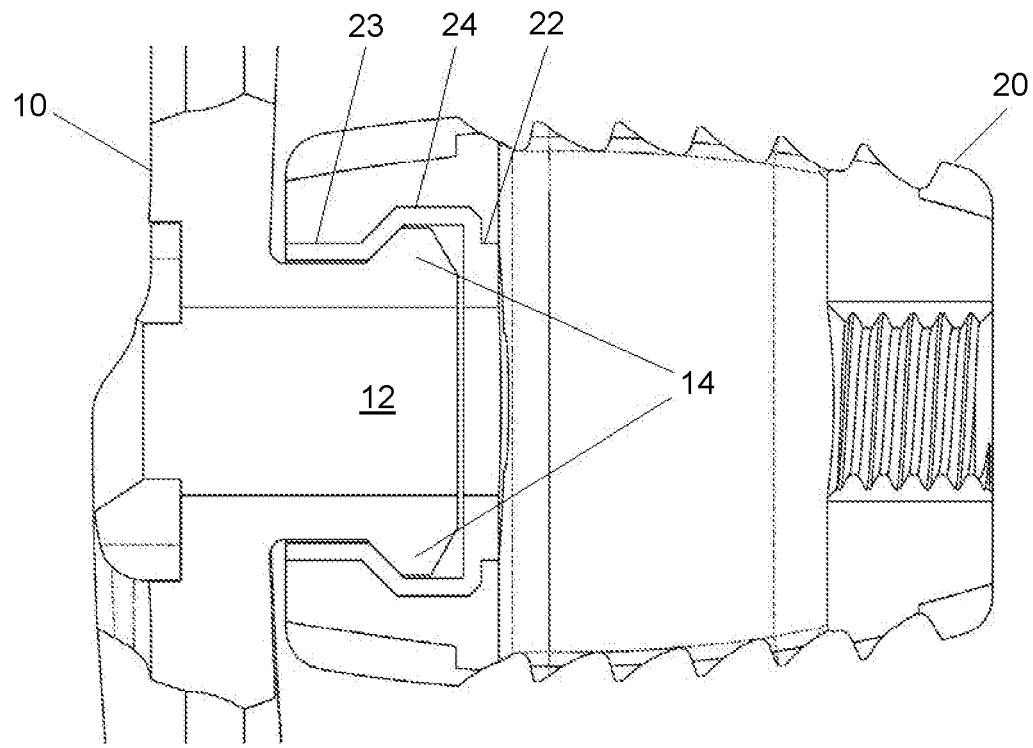
FIG. 8 is a side sectioned view of a bone fixation plate and an implant.

In FIG. 8 is a side sectioned view of the fixation plate 10 and implant 20 in a locked position. In the locked position, the pins 24 extending radially from the cylindrical member 12 provide a surface that is in excess of the diameter of the outer portion 23 of the attachment port 22. The pins 24 provide a surface that can be less than the diameter of the inner portion 24 of the attachment port 22 to allow the fixation plate 10 to rotate relative to the implant 20 without encumbrance. While the inner portion 24 is shown as being cylindrical with a substantially equal diameter throughout, in some embodiments the inner portion 24 can be non-cylindrical or have a varying diameter. In some embodiments, the inner portion 24 further comprises a varying diameter with at least one area with a diameter smaller than the distance between the distal ends of the pins 24. In some embodiments, the inner portion 24 further comprises at least one area where material has been added to create a localized area with a diameter smaller than the distance between the distal ends of the pins 24. The use of areas with a diameter smaller than the distance between the distal ends of the pins 24 can be used to provide rotational stops for the fixation plate 10 relative to the implant 20.

Figure 9:
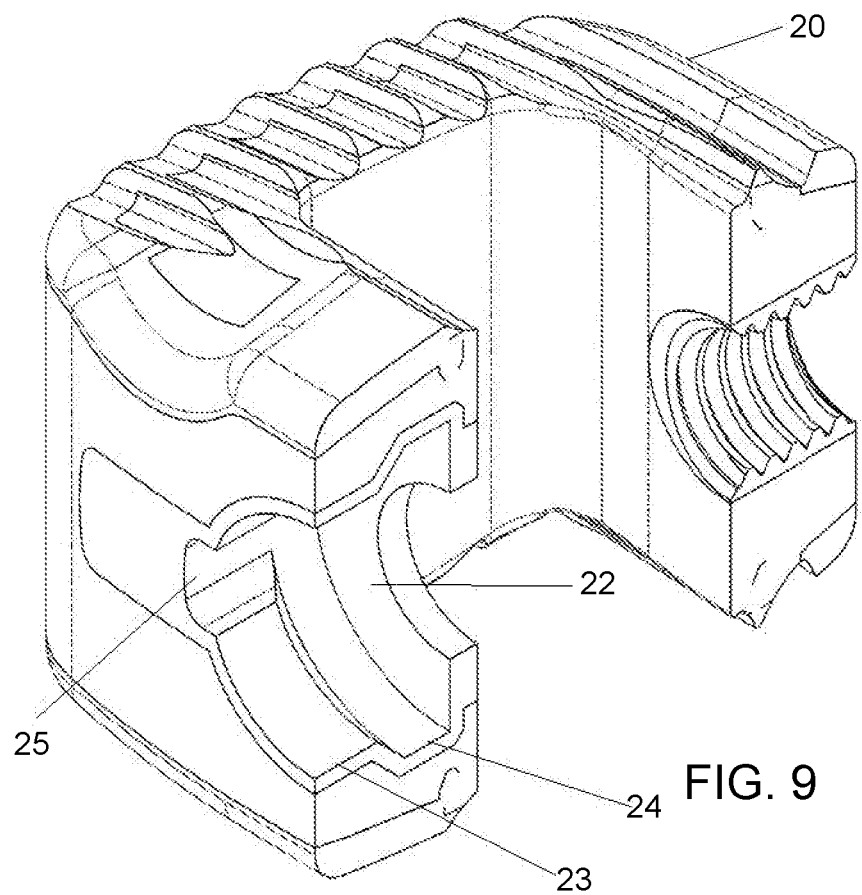
FIG. 9 is an isometric sectioned view of an implant configured to receive the bone fixation plate.
Figure 10:
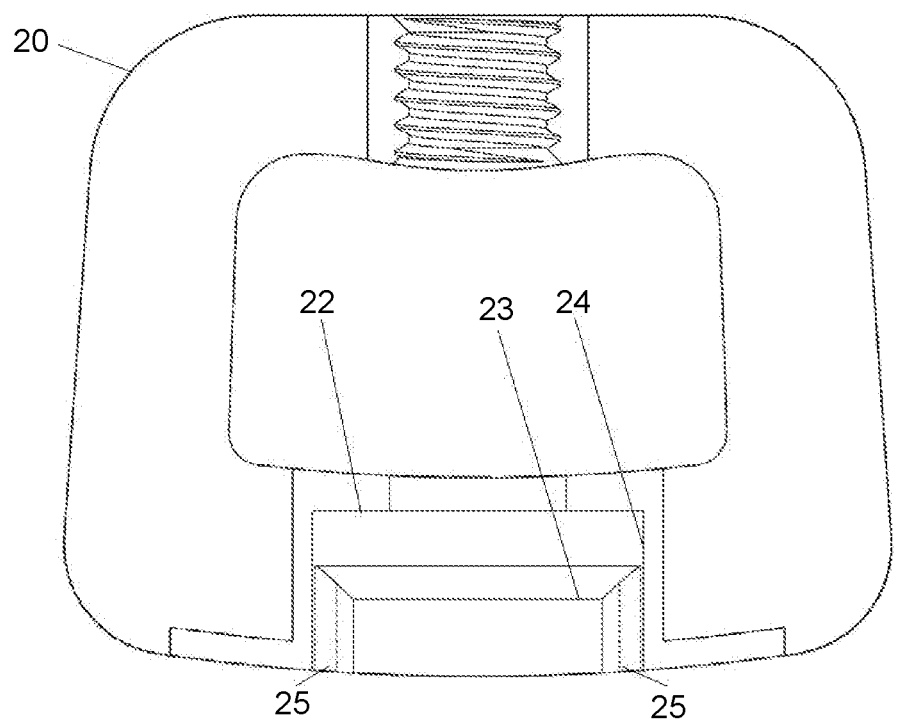
FIG. 10 is a top sectioned view of an implant configured to receive the bone fixation plate.

In FIG. 9 is an isometric sectioned view of the implant 20 configured to accept the fixation plate 10. In FIG. 10 is a top sectioned view of the implant 20 configured to accept the fixation plate 10. These figures provide additional views of the attachment port 22 and the exemplary configuration using an outer portion 23, an inner portion 24 and cutouts 25.

What has been described is a fixation plate and an implant configured to accept the disclosed fixation plate. In this disclosure, there is shown and described only an exemplary embodiment of the invention, but, as aforementioned, it is to be understood that the invention is capable of use in various other combinations and environments and is capable of changes or modifications within the scope of the inventive concept as expressed herein.

The invention claimed is:

1. A medical implant system, comprising:
   a bone fusion implant configured for implantation into a body, wherein the bone fusion implant comprises at least one side;
   one or more fasteners configured to fix the bone fusion implant to one or more bony structures in the body; and
   an elongate plate comprising a plurality of openings configured to allow passage of the one or more fasteners through the elongate plate, the elongate plate being rotationally fixed to a side of the bone fusion implant and configured to rotate relative to the bone fusion implant and allow axial compression relative to the bone fusion implant after implantation into the body, wherein an amount of the axial compression is adjustable based on placement of the one or more fasteners relative to the elongate plate and an angle of the elongate plate relative to the bone fusion implant.

2. The medical implant system of claim 1, wherein the plurality of openings are further configured to rotate about the one or more fasteners.

3. The medical implant system of claim 1, wherein the plurality of openings further comprise a smooth annular shape with a first diameter and each of the one or more fasteners further comprises a head with a smooth annular shape with a second diameter; wherein the second diameter is less than the first diameter.

4. The medical implant system of claim 1, wherein the bone fusion implant further comprises a forward and rear direction, a lateral direction and an axial direction.

5. The medical implant system of claim 4, wherein the elongate plate further comprises a fixed position in a forward to rear direction relative to the bone fusion implant and is configured to rotate about an axis in the forward to rear direction of the bone fusion implant.

6. The medical implant system of claim 1, wherein the elongate plate is configured to allow at least one degree of freedom relative to the bone fusion implant and the degree of freedom relative to the bone fusion implant further comprises the axial direction.

7. The medical implant system of claim 1, wherein the elongate plate further comprises a quarter turn fastener extending towards the side of the bone fusion implant; and wherein the bone fusion implant further comprises an opening corresponding to the quarter turn fastener located on the elongate plate.

8. The medical implant system of claim 1, wherein the elongate plate is further translationally fixed relative to the bone fusion implant in all directions and rotationally free in at least one direction relative to the bone fusion implant.

9. The medical implant system of claim 1, wherein the plurality of openings comprise equidistantly distributed openings.

10. The medical implant system of claim 9, wherein the amount of axial compression is a function of an angle of the elongate plate relative to the bone fusion implant and a distance between at least two adjacent openings in the plurality of openings.

11. The medical implant system of claim 10, wherein the amount of axial compression is correlated with the angle of the elongate plate for the distance between the at least two adjacent openings in the plurality of openings.

12. The medical implant system of claim 1, wherein an angle of rotation of the elongate plate relative to the bone fusion implant is a function of an interference between the bone fusion implant and the one or more fasteners through the elongate plate.

13. The medical implant of claim 1, wherein the elongate plate is configured to allow at least one degree of freedom relative to the bone fusion implant.

* * * * *